US007204823B2

(12) United States Patent
Estes et al.

(10) Patent No.: US 7,204,823 B2
(45) Date of Patent: Apr. 17, 2007

(54) MEDICATION DELIVERY SYSTEM AND MONITOR

(75) Inventors: Mark C. Estes, Simi Valley, CA (US); Leif N. Bowman, Burbank, CA (US); Denetta Malave, Valencia, CA (US); Cary Dean Talbot, Saugus, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 10/025,052

(22) Filed: Dec. 19, 2001

(65) Prior Publication Data

US 2003/0114836 A1    Jun. 19, 2003

(51) Int. Cl.
A61M 31/00    (2006.01)
(52) U.S. Cl. ........................................................ 604/65
(58) Field of Classification Search ................. 604/65, 604/66, 67, 30–34, 218, 131, 154; 128/DIG. 1, 128/DIG. 12, DIG. 13
See application file for complete search history.

(56) References Cited

U.S. PATENT DOCUMENTS

| 3,701,345 | A |   | 10/1972 | Heilman et al. |
| 4,457,751 | A | * | 7/1984  | Rodler ............................. 604/66 |
| 4,513,796 | A | * | 4/1985  | Miller et al. ...................... 141/83 |
| 4,562,751 | A |   | 1/1986  | Nason et al. |
| 4,619,646 | A |   | 10/1986 | Fernández-Tresguerres Hernandez et al. |
| 4,678,408 | A |   | 7/1987  | Nason et al. |
| 4,685,903 | A |   | 8/1987  | Cable et al. |
| 4,731,051 | A | * | 3/1988  | Fischell ........................... 604/67 |
| 4,747,824 | A |   | 5/1988  | Spinello |
| 4,756,706 | A | * | 7/1988  | Kerns et al. ..................... 604/66 |
| 5,034,004 | A | * | 7/1991  | Crankshaw .................... 604/154 |
| 5,080,653 | A |   | 1/1992  | Voss et al. |
| 5,097,122 | A |   | 3/1992  | Colman et al. |
| 5,207,642 | A | * | 5/1993  | Orkin et al. .................... 604/65 |
| 5,219,099 | A |   | 6/1993  | Spence et al. |
| 5,376,070 | A |   | 12/1994 | Purvis et al. |
| 5,569,186 | A |   | 10/1996 | Lord et al. |
| 5,609,575 | A | * | 3/1997  | Larson et al. .................. 604/65 |
| 5,665,065 | A |   | 9/1997  | Colman et al. |
| 5,697,407 | A | * | 12/1997 | Lasonde ....................... 141/104 |
| 5,713,856 | A | * | 2/1998  | Eggers et al. .................. 604/65 |
| 5,733,259 | A |   | 3/1998  | Valcke et al. |
| 5,772,635 | A | * | 6/1998  | Dastur et al. ................. 604/131 |

(Continued)

FOREIGN PATENT DOCUMENTS

DE    2240694    3/1973

(Continued)

*Primary Examiner*—Manuel Mendez
(74) *Attorney, Agent, or Firm*—Gates & Cooper LLP

(57) ABSTRACT

Systems and methods for the delivery and monitoring of a medication, such as insulin, to a recipient are provided. An exemplary feature-rich system comprises an infusion pump with a control system for controlling medication delivery by the infusion pump and a bolus estimator for estimating an appropriate amount of medication for delivery by the control system with the infusion pump. Estimating the appropriate amount of medication for delivery is based upon one or more settings which each vary according to a setting profile. In other embodiments, the control system comprises a suspend function for temporarily suspending medication delivery by the infusion pump, an alarm profile function for programming a variable alarm volume of the alarm and a simplified menu for controlling the dual wave bolus delivery function.

98 Claims, 10 Drawing Sheets

U.S. PATENT DOCUMENTS

| | | | |
|---|---|---|---|
| 5,848,988 A * | 12/1998 | Davis | 604/65 |
| 5,935,099 A * | 8/1999 | Peterson et al. | 604/65 |
| 6,231,560 B1 | 5/2001 | Bui et al. | |
| 6,562,001 B2 * | 5/2003 | Lebel et al. | 604/65 |
| 6,565,535 B2 * | 5/2003 | Zaias et al. | 604/152 |
| 6,659,948 B2 * | 12/2003 | Lebel et al. | 600/300 |
| 6,810,290 B2 * | 10/2004 | Lebel et al. | 607/60 |

FOREIGN PATENT DOCUMENTS

| | | |
|---|---|---|
| DE | 43 29 229 A1 | 3/1995 |
| DE | 198 42 722 A1 | 4/2000 |
| EP | 0 806 738 A1 | 11/1997 |
| WO | WO 00/10628 | 3/2000 |

* cited by examiner

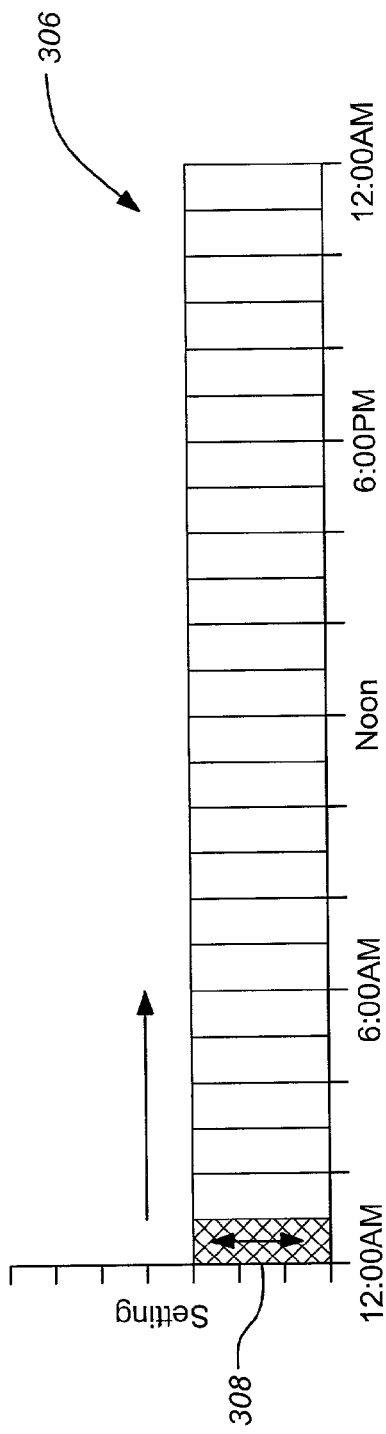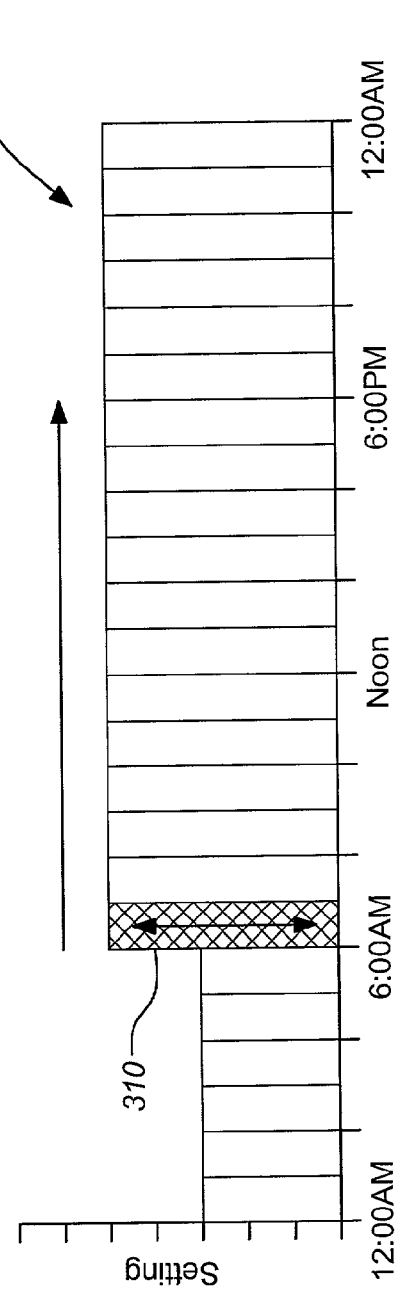

MEDICATION DELIVERY SYSTEM AND MONITOR

BACKGROUND OF THE INVENTION

1. Field of the Invention

This invention relates generally to systems for delivering and monitoring medications. More specifically, this invention relates to methods and systems for the infusion of insulin.

2. Description of the Related Art

Infusion devices and systems are well-known in the medical arts for delivering or dispensing a medication to a patient, such as insulin to a diabetic. Generally such devices include a reservoir containing a medication for administration to the patient, an infusion pump for dispensing a medication (typically through infusion tubing and an associated catheter) and control and monitoring systems to facilitate the accurate delivery of the medication.

Infusion pumps typically include a small drive motor connected to a reservoir piston to administer the medication to the user. Programmable controls can be provided for operating the drive motor continuously or at periodic intervals to obtain a closely controlled and accurate delivery of the medication over an extended period of time. Exemplary infusion pumps that are used to administer insulin and other medications are shown and described in U.S. Pat. Nos. 4,562,751; 4,678,403; 4,685,903; 5,080,653 and 5,097,122, and U.S. patent application Ser. No. 09/334,858 (now U.S. Pat. No. 6,554,798), filed Jun. 16, 1999, entitled "EXTERNAL INFUSION DEVICE WITH REMOTE PROGRAMMING BOLUS ESTIMATOR AND/OR VIBRATION ALARM CAPABILITIES", all of which are incorporated herein by reference.

Infusion devices provide significant advantages over manual administration by accurately delivering insulin or other medications over an extended period of time. Infusion devices can be relatively compact as well as water resistant, and may thus be adapted to be carried by the user, for example, by means of a belt clip. Typical compact infusion devices include a housing adapted to be worn on a belt, to be contained within a clothing pocket, to be worn under clothing (e.g. for concealment under clothing in a generally unobtrusive manner) and/or to be worn against the skin. As a result, medication can be delivered to the user with precision and in an automated manner, without significant restriction on the user's mobility or lifestyle, including the ability to participate in water sports.

SUMMARY OF THE INVENTION

Embodiments of the invention disclosed herein provide monitors and delivery systems which allow for the an enhanced control of the delivery of a medication. A typical embodiment of the present invention includes an infusion pump, a control system for controlling medication delivery from the infusion pump and a bolus estimator for estimating an appropriate amount of a medication such as insulin or the like for delivery by the control system via the infusion pump, where estimating the appropriate amount of the medication for delivery is based upon one or more settings which can be varied according to a setting profile. For example, a control system can control medication delivery according to one or more medication delivery profiles. In preferred embodiments, medication delivery profiles are designed to optimize the delivery of an appropriate amount of insulin that is estimated by the bolus estimator. Such medication delivery profile settings can include additional settings relating to factors such as target blood glucose, carbohydrate ratio and/or insulin sensitivity. In one embodiment, the setting profile for at least one setting, such as target blood glucose, carbohydrate ratio or insulin sensitivity, includes a value which varies according to a schedule.

In preferred embodiments of the invention, the bolus estimator estimates the appropriate amount of insulin based upon one or more event markers stored in a memory of the device. The one or more event markers can track physiological events which affect insulin need, such as meals, medication status, activities or general health. Such embodiments can include a wide variety of markers such as a meal marker, a snack marker, a high blood glucose marker, a low blood glucose marker, an exercise marker, an illness marker and/or a stress marker.

Another embodiment of the invention includes a control system for controlling medication delivery from the infusion device. Such control systems can be tailored to the requirements of a specific pathology. In an illustrative embodiment, a control system includes a suspend function for temporarily suspending medication delivery from the infusion device. In preferred embodiments of the invention, medication delivery is controlled using two or more medication delivery profiles, such as wave profiles. Exemplary wave profiles include a square wave bolus profile, a dual wave bolus profile or a basal profile. In a preferred embodiment of the invention, the control system includes a suspend function for separately suspending medication delivery based on the wave profiles. In another embodiment, the control system further includes a resume function for selectively restarting a wave profile. In such systems, a compensating function can also be used for delivering a compensating bolus to account for any suspended wave profile. The suspend function can further include a full suspend function for directly suspending all delivery of a medication.

In yet another embodiment of the invention, the suspend function includes a menu system for selecting a period of time for temporarily suspending medication delivery from the infusion pump. The menu system can include, for example, an array of fixed periods from which to select a period of time for temporarily suspending medication delivery. In preferred embodiments, the menu system can also include one or more selectable increment periods to modulate the period of time for temporarily suspending medication delivery. In another embodiment, the menu system includes a specified time of day to select as an end of the period of time for temporarily suspending medication delivery. In some embodiments of the invention, after a period of time for temporarily suspending medication delivery has concluded, the pump automatically resumes medication delivery.

In a related embodiment of the invention the suspend function includes a block function for preventing delivery of medication after a potentially harmful amount of medication is requested by a user. The potentially harmfully amount of medication can result, for example, from a request for an unusually large bolus, a bolus requested too soon after a previous bolus is delivered, or, alternatively, a request for too low of a total medication dose. Such functions typically include a warning signal to the user of the potentially harmful amount of medication requested. In one embodiment, the block function can be triggered in situations where a medication measurement that is integrated over an integration period (e.g., the period of time in which a measured amount of medication is infused) exceeds a target value. In another embodiment, the block function can be triggered in situations where a second medication measurement that is integrated over a simultaneous and overlapping integration period exceeds a target value. The integration period can further be subdivided into a plurality of subperiods where each subperiod is associated with a subtotal representing medication delivered. In one embodiment of the invention, the oldest subtotal of the subperiods can be replaced by the newest subtotal of the subperiods to, for example, identify a possible overmedication.

In yet another embodiment of the invention the infusion pump includes an alarm to provide information on the status of the infusion pump and a control system for controlling medication delivery from the infusion pump. For example, the control system can include an alarm profile function for programming a variable alarm volume of the alarm. In one embodiment, the variable alarm volume can be set by the user. In a related embodiment, the alarm profile function varies the alarm volume according to a preselected schedule.

Another embodiment of the invention includes an infusion pump and a control system for controlling medication delivery by the infusion pump including a dual wave bolus delivery function, where the control system includes a conventional menu for controlling the dual wave bolus delivery function (e.g., a menu identifying parameters associated with a wave bolus delivery function which may be set by the user). In a related embodiment, the control system includes a conventional or simplified menu for controlling the dual wave bolus delivery function (e.g., a menu identifying one or more preset parameters associated with a dual wave bolus). Embodiments of the invention include those where the simplified menu and the conventional menu can be alternately selected. In preferred embodiments of the invention, the simplified menu includes a single entry of a total medication volume that can be divided by a preset ratio into a first wave bolus and a second wave bolus and then delivered with a preset delay time between the first wave bolus and the second wave bolus. In other preferred embodiments of the invention, the preset ratio and preset delay time can include default values set in a pump setup menu. The control system can also include one or more additional delivery functions and a default delivery mode selected in the pump setup menu from the dual wave bolus delivery function and/or the additional delivery functions disclosed herein. Examples of such delivery functions include a square wave bolus delivery function and a basal delivery function.

In preferred embodiments of the invention, the control system is programmed to control medication delivery from an RF programmer, a communication station and/or direct manual input. In another embodiment of the invention, a first device of an infusion device and RF remote pair can be used to find the second device by activating a find function in the first device to induce an audible signal from the second device.

BRIEF DESCRIPTION OF THE DRAWINGS

Referring now to the drawings in which like reference numbers represent corresponding parts throughout:

FIGS. 3B–3D illustrate a graphical programming interface for setting profiles;

DETAILED DESCRIPTION OF THE PREFERRED EMBODIMENTS

1. Overview

Embodiments of the present invention encompass methods and systems for the convenient operation of medication infusion devices. The description provided herein encompasses the architecture of the apparatus, associated features which optimize the control and convenience of such devices and methods for their utilization. Features which optimize the control and convenience of the devices of the present invention may be implemented in a wide range of infusion device designs known in the art.

A typical embodiment of the present invention includes an infusion pump, a control system for controlling medication delivery from the infusion pump and a bolus estimator for estimating an appropriate amount of a medication such as insulin or the like for delivery by the control system via the infusion pump. In preferred embodiments, a function of estimating the appropriate amount of the medication for delivery is based upon one or more settings (e.g., a variable parameter that can be used to control the delivery of a medication) which can be varied according to a setting profile (e.g., a prescribed relationship between the setting and a variable, such as another setting or a schedule). Typically, the control system controls medication delivery according to one or more medication delivery profiles (e.g., setting profiles for a medication delivery rate that varies according to a schedule). In preferred embodiments the medication delivery profiles are designed to optimize the delivery of an appropriate amount of insulin that is estimated by the bolus estimator. In highly preferred embodiments, the setting profile for at least one setting, such as target blood glucose, carbohydrate ratio or insulin sensitivity, includes a value that varies according to a schedule. In other preferred embodiments of the invention, the bolus estimator estimates the appropriate amount of insulin based upon one or more event markers stored in a memory of the device (e.g., the recordation of when a earlier bolus was administered).

Figure 1:
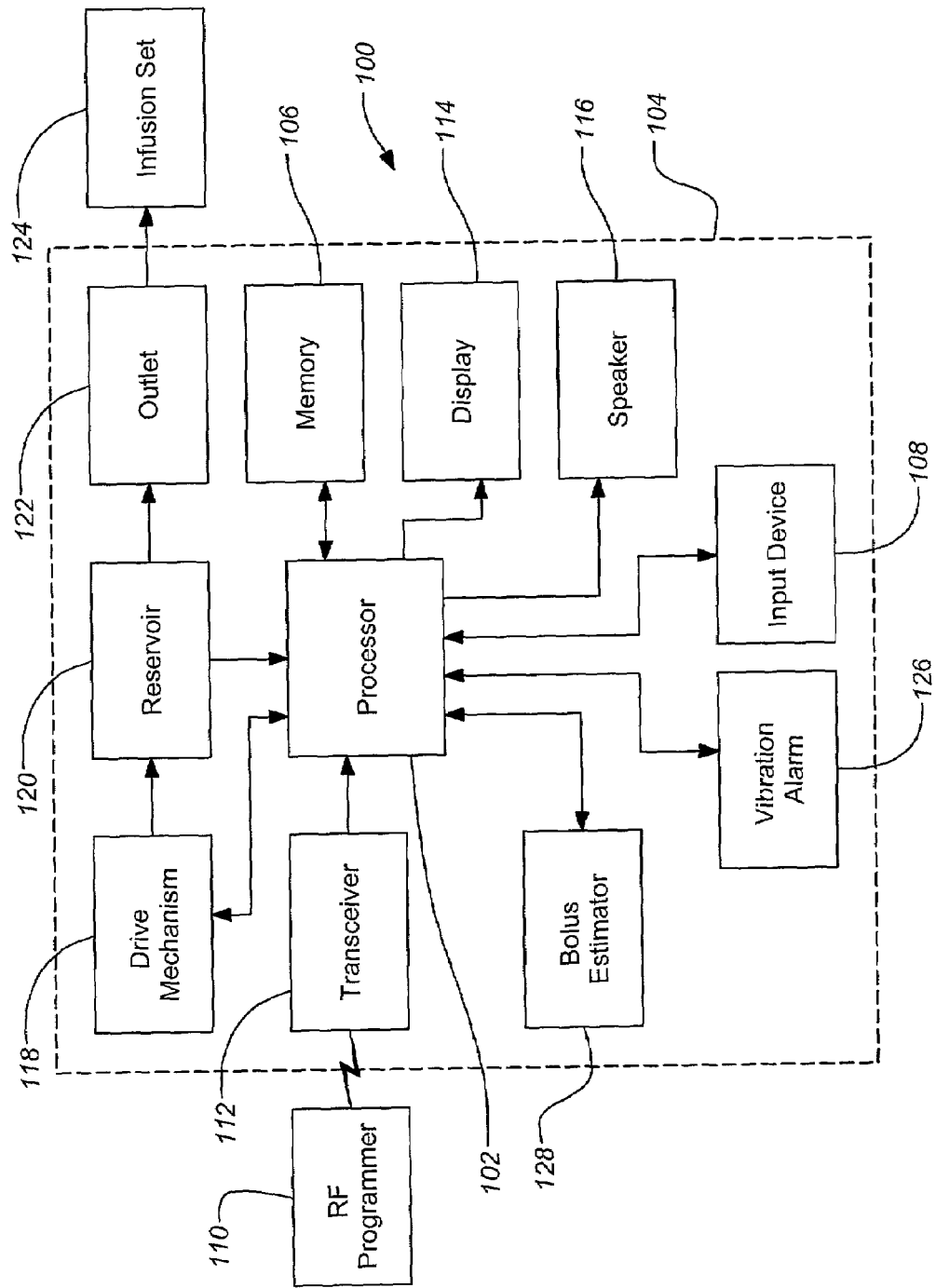
FIG. 1 is a block diagram of an exemplary infusion device embodiment of the invention.

FIG. 1 illustrates a typical infusion device 100 of the present invention. A processor 102 contained in a housing 104 of the device 100 controls the operation of the infusion device 100. The processor 102, connected to internal memory 106, can be used to run programs that control the infusion device 100. The memory 106 stores programs, historical data, user defined information, settings and other parameters. In one embodiment the memory can be a flash memory and SRAM. In alternative embodiments, the memory 106 may include other memory storage devices such as ROM, DRAM, RAM, EPROM, and dynamic storage such as other flash memory and magnetic media and similar devices. In one embodiment the infusion device 100 can be programmed directly through a manual input device 108, such as a keyboard or touch screen input, built directly into the device. The device 100 can include (or alternatively include) programmability through commands received from a radio frequency (RF) programmer 110 through an RF transceiver 112 built into the device 100. Feedback from the device 100 on the status or programming changes are displayed on a display 114, such as an liquid crystal display (LCD) or touch screen display, and/or audibly through a speaker 116. The RF programmer typically includes an input device of some type, such as a simple keypad, and may also include a display and/or speaker to provide feedback in a manner similar to the infusion device 100.

In preferred embodiments of the invention, the processor 102 can be coupled to a drive mechanism 118 that can be connected to a medication or fluid reservoir 120 containing fluid that can be directed through an outlet 122 in the reservoir 120 and housing 104, and then into a body of a user through tubing and an infusion set 124. In other embodiments, the input device 108, display 114 and/or speaker 116 can be omitted from the external infusion device 100, with all programming and data transfer being handled through the RF programmer 110. In further embodiments, the infusion device 100 can deliver fluid directly to the user without tubing or an infusion set 124. For example, the infusion device 100 can be located on the user's body at the infusion site.

In an illustrative embodiment of the invention, the infusion device 100 can be a medication infusion pump capable of delivering insulin to a diabetic at a rate of about 0 to about 35 units/hour in basal rates and up to about 25.0 units per meal bolus of U-100 insulin. In related embodiments, the infusion pump delivers other concentrations of insulin and/or other medications and may operate at other rates. Alternative embodiments of the invention can deliver other fluid compositions such as saline, as well as fluids that include agents such as vitamins, medications, drugs, peptides, hormones, proteins, enzymes, and vaccines, or the like.

The external infusion device 100 can provide the user with an alarm signal as a warning to indicate some situation to address such as a low reservoir condition or low battery or some malfunction of the system (e.g., an occlusion of the outlet that restricts the delivery of the fluid). In one embodiment of the invention, the user has the choice of an audible alarm through the speaker 116 and/or a vibration alarm 126. Alarms may start out at a low level and escalate until acknowledged by the user. In further embodiments, both an audible alarm and a vibration alarm 126 may be given at the same time.

Embodiments of the invention can also include a bolus estimator 128 which may operate as an independent unit within the device or as a program run by the processor 102. The bolus estimator 128 can function as a specialized calculator, providing values for estimating the insulin needs of the patient and simplifying the management of the administration of insulin to the patient. For example, some settings for the bolus estimator 128 are a target blood glucose value, units of blood glucose measurement (e.g., mmol/l or mg/dl), units of carbohydrate, the carbohydrate to insulin ratio, insulin sensitivity and blood glucose lockout (a block, requiring a minimum time delay before the bolus may be adjusted to allow the previous estimate to act).

In embodiments of the present invention, profiles can be applied to a wide range of settings to facilitate versatile control of the infusion device 100. Numerous settings govern control of the infusion device. Some settings are directed to the actual administration of medication, such as the delivery rate, blood glucose level, carbohydrate to insulin ratio or insulin sensitivity. Other settings direct more mundane aspects of the operation of the infusion device, such as alarm volume. Any infusion device setting can be controlled according to a profile. A setting that uses a profile can vary according to at least one other condition or input. For example, a setting can operate by a profile that varies in value according to a daily schedule. In this case, the other condition is time. Profiles can be used to vary the medication delivery rates (e.g., medication delivery profiles), which can be described as waves. Although, schedule-based setting profiles are preferred, setting profiles can also be used which vary according to other settings, such as blood glucose (BG) or carbohydrate measurements.

Medication delivery by the infusion device 100 is preferably managed through the use of profiles which represent a varying medication delivery rate over a fixed period of time. Multiple programming options can be available in the infusion device 100, and preferably includes at least two customized basal profiles, a carbohydrate (or bolus) estimator 128 and an alarm clock, as well as remote and/or on-device programming.

Figure 2:
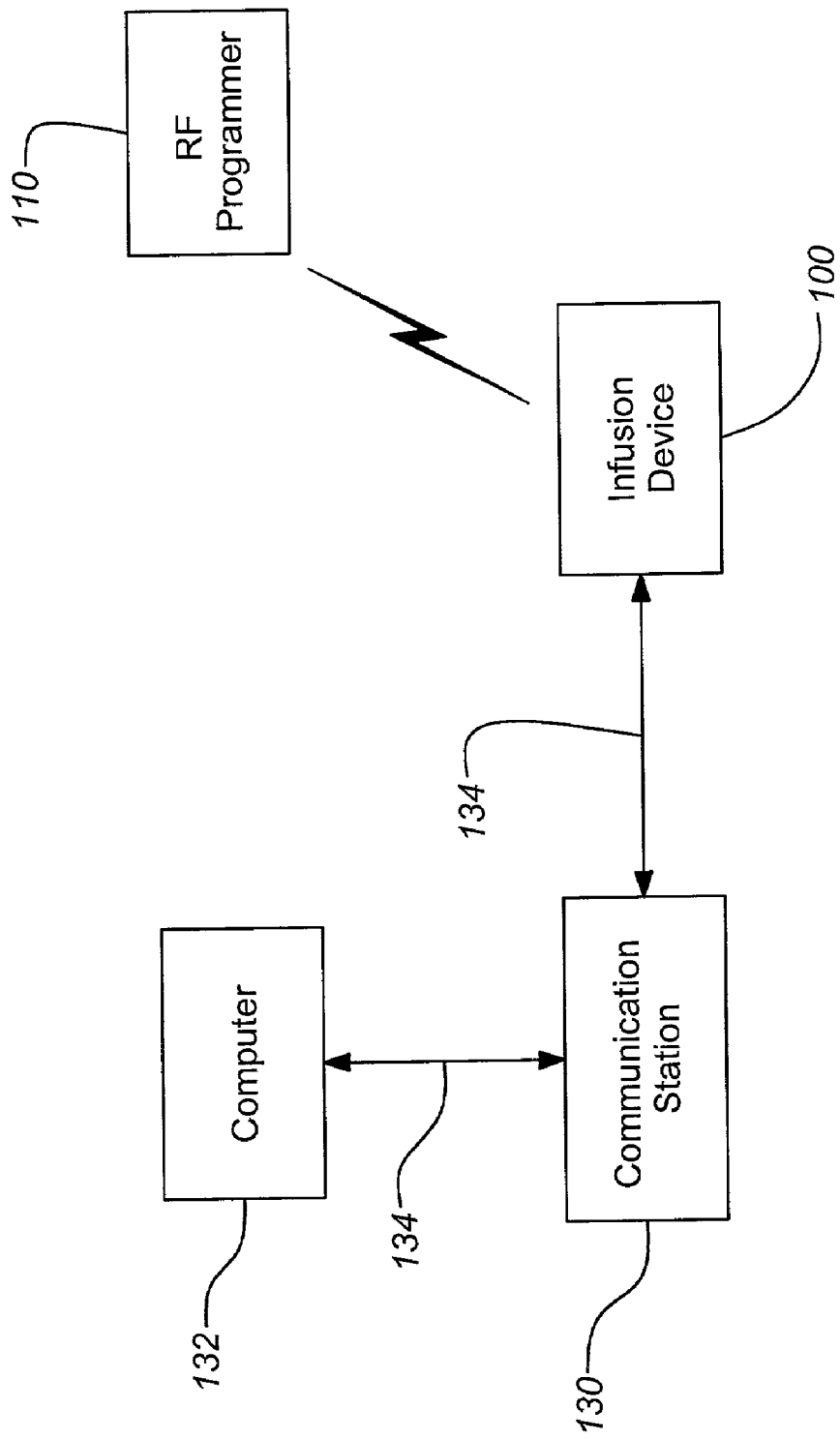
FIG. 2 is a block diagram of the infusion device configured through a communication station.

FIG. 2 is a block diagram of the infusion device configured through a communication station 130. A physician/educator can configure the external infusion device 100 through a communication station 130 to provide or restrict access to certain programming options. In preferred embodiments, an external infusion device 100 can download stored information through the communication station 130. A description of a communication station of this general type is found in U.S. Pat. No. 5,376,070 to Purvis et al., entitled "DATA TRANSFER SYSTEM FOR AN INFUSION PUMP" and U.S. patent application Ser. No. 09/409,014, filed Sep. 29, 1999 (PCT publication WO 00/18449) to Malave et al., entitled "COMMUNICATION STATION AND SOFTWARE FOR INTERFACING WITH AN INFUSION PUMP, ANALYTE MONITOR, ANALYTE METER OR THE LIKE", which are both incorporated herein by reference. Such information can be used alone or in combination with information from a glucose sensor and/or a glucose meter (not shown) to assist the user and/or the health care professional in making intelligent therapy decisions. Moreover, the information, programs and data may be downloaded to a remote or local PC, laptop, communication station, or the like, for analysis and review by trained professional through the transceiver 112. The data may also be downloaded through a communication station 130 to a remotely located computer 132 such as a PC, laptop, or the like, over communication lines 134, such as by wired, modem, wireless connection or other electronic communication methods.

Operation of the infusion device 100 is typically directed through programming which can be derived from a variety of possible sources. The programming can either be entered directly into the infusion device 100 (e.g., on the input device 108), received via the RF programmer 110, or transferred from the communication station 130 (originating, for example, in the computer 132). In one embodiment, the infusion device maintains an event log in the memory 106 that includes the source of programming. This information can be used to study trends in the use of the infusion device 100 as well as to quickly diagnose the source of flawed programming.

The external infusion device 100 can also have additional memory capacity to allow configuring of the display during manufacturing to display information in several different foreign languages, and allow for future upgrades and revisions without the requirement of a hardware change. For example, a PC program can enable manufacturing to select the language for the pump. Languages can include English, French, Spanish, Italian, Dutch, Swedish and German. In alternative embodiments, other languages can be determined based upon market selection.

2. Bolus Estimator

Physiological carbohydrate levels are a predominant, but not exclusive factor affecting blood glucose levels. The bolus estimator 128 of the invention (or carbohydrate estimator that estimates a bolus based on carbohydrate consumption (CHO)) can assist the user with carbohydrate counting and in determining precise dosing adjustments to account for meals. Generally, it is sufficient to account just for the carbohydrates. It also encourages the user to enter current blood glucose values before using this feature, which increases compliance with medical regimens and optimizes control of medical devices. In certain embodiments of the invention, the bolus estimator 128 in the external infusion device 100 can be connected or coupled to a glucose monitor by way of the RF programmer 110 (or other data transfer mechanism) to provide direct input to the bolus estimator 128.

In preferred embodiments of the invention, the bolus estimator 128 is used to assist the external infusion device 100 user with the estimations to determine the proper bolus amount needed to cover an anticipated carbohydrate intake at meals. The bolus estimator 128 can effect this by suggesting a bolus based on a pre-programmed carbohydrate ratio that can be stored in the memory 106 of the external infusion device 100. The bolus estimator 128 can also take into account the user's insulin sensitivity and the differential between the user's pre-programmed target blood glucose (BG) level and the user's current BG level at the time the carbohydrate estimator 128 is activated. In this context, the recommendation, or result of the bolus estimator 128, is sometimes referred to as a "correction bolus".

The bolus estimator 128 is generally activated by the user or the health care professional in a setup menu of the external infusion device 100, before it is operational, and preferably after the user has demonstrated a sufficient understanding of how to estimate carbohydrate intake. In preferred embodiments, the bolus estimator 128 is activated and programmed by using the input device 108 on the external infusion device 100. In some embodiments, the bolus estimator 128 may be alternately programmed and activated with an RF programmer 110. In other embodiments, the current glucose readings for the user can be provided by receipt of the medication level measurement from a glucose monitor or via the RF programmer 110 to facilitate a correction for changing blood glucose (BG) levels. Descriptions of correcting infusion rates based on blood glucose readings may be found in U.S. Pat. No. 5,569,186 to Lord et al., entitled "CLOSED LOOP INFUSION PUMP SYSTEM WITH REMOVABLE GLUCOSE SENSOR,"; U.S. Pat. No. 5,665,065 to Colman et al., entitled "MEDICATION INFUSION DEVICE WITH BLOOD GLUCOSE DATA INPUT"; and U.S. patent application Ser. No. 09/334,858, filed Jun. 16, 1999 and entitled "EXTERNAL INFUSION DEVICE WITH REMOTE PROGRAMMING BOLUS ESTIMATOR AND VIBRATION ALARM CAPABILITIES"; which are all herein incorporated by reference.

In alternative embodiments of the invention, the user may be able to use other combinations of the values to identify different bolus types and amounts. In other embodiments, the bolus estimator 128 can be used in a closed-loop system to augment the readings or check the closed-loop system's capability based on carbohydrate estimated meals. In other embodiments, the bolus estimator 128 may be used to calculate correction boluses based on other parameters, with the type of bolus corrections being determined by the medication being infused, physiological characteristics of the user or the like. Preferably, the bolus estimator 128 uses stored values or parameters related to the individual and current values, parameters or measurements applied to an algorithm to provide a recommended bolus that can be accepted, modified or rejected by the user. For instance in situations of premature labor in pregnancy, the measurement of the contraction rate may be used to suggest a bolus of tocolysis medication. In HIV, a bolus amount of medication being infused may be adjusted based on a relationship to the current viral loads in the patient. In stroke or cardiac cases, the coagulation rate may be used to determine the bolus amount of heparin to be administered. Other calculations may be made and the invention is not limited to the above-described examples.

After the bolus estimator 128 has been enabled, the user can be prompted to store values for the following properties in the memory 106 of the external infusion device 100: the target blood glucose, insulin sensitivity and the carbohydrate ratio. In alternative embodiments, more or fewer properties may be needed or used by the bolus estimator 128. These values are used by the bolus estimator 128 and the processor 102 of the external infusion device 100 to perform the necessary calculations in suggesting a bolus amount. In preferred embodiments, access to programming and changing these values may be restricted to a health care professional. In other embodiments, these values can be restricted to entry through an RF programmer 110 or a connection of the external infusion device 100 with a programming device, such as a PC, laptop or the like. Examples of inputted values to be stored for the bolus estimator 128 are provided below.

Target blood glucose (Target) is the target blood glucose (BG) that the user would like to achieve and maintain. Generally, the programmable blood glucose (BG) values for this range are between 60 to 200 in five-unit increments. Preferably, the carbohydrate calculator has the capability to accept values that; range between 20 to 600 in 1-unit increments to cover a large number of possible scenarios. In alternative embodiments, different ranges and increments may be used.

Insulin sensitivity (Set Sens) is a property that reflects how far the user's blood glucose drops in milligrams per deciliter (mg/dl) when one unit of insulin is taken. Typically, the programmable values for this range are between 5 to 180 in one unit increments. However, in alternative embodiments, different ranges and increments may be used. In other embodiments, insulin sensitivity can be programmable for multiple different time periods (e.g., up to four different periods), the use of which can require multiple separate profiles to be stored in the memory 106. Setting the Insulin sensitivity profiles can be similar to setting the basal profiles. In alternative embodiments, more or fewer time periods (and corresponding profiles) may be used.

The carbohydrate ratio (Set Carbs) is a value that reflects the amount of carbohydrates that are covered by one unit of insulin. Generally, the values are in the range of 1 to 300 in increments of 1 unit (or, alternatively, in ranges of 0.1 to 5.0 in increments of 0.1 for carbohydrate exchanges). Preferably, the programmable values for this range are between 5 to 30 in one unit increments. However, in alternative embodiments, different ranges and increments can be used.

As a safety precaution, the user or healthcare professional may also set a Lockout Period, which takes into account the pharmacokinetic effect of insulin when suggesting a bolus. The purpose is to prevent a successive use of a correction bolus when the pharmacokinetic effects of the previous bolus have not yet been accounted for. The programmable values for this range are between 30 minutes to 240 minutes, programmable in 15 or 30 minute increments. However, in alternative embodiments, different ranges and increments may be used. In further alternative embodiments, the lock out period may be automatically calculated based on boluses recently delivered and/or canceled based on new blood glucose (BG) readings. In other embodiments, the carbohydrate calculator 118 may include a programmable reminder to check the post-prandial blood glucose value to determine if additional boluses and or corrections should be made at a later time after the meal. The programmable reminder values are between 30 minutes to 240 minutes, programmable in 15 or 30 minute increments. In alternative embodiments, different values and increments may be used.

After the properties are set in the memory 106 of the external infusion device 100, the bolus estimator 128 can suggest a bolus based on the entry of the estimated carbohydrate intake and current and target blood glucose (BG) levels. The calculation can be performed using the three properties programmed and stored in the memory 106. Preferred embodiments use the following equation:

$$\text{Bolus} = \frac{\text{Current BG} - \text{Target BG}}{\text{Insulin Sensitivity}} + \frac{\text{Carbohydrates to be Consumed}}{\text{Carbohydrate Ratio}}$$

In contexts where the user wishes the external infusion device 100 to suggest a bolus for the estimated carbohydrate intake only, then the only value to program is the carbohydrate ratio, and the BG portion of the equation can be ignored. In alternative embodiments, variations or different equations can be used.

In operation, once the bolus estimator 128 has been enabled and the above listed values have been programmed into the memory 106 of the external infusion device 100, the bolus estimator 128 can be used to suggest a correction or meal bolus. The user may then accept or change the bolus amount suggested by the bolus estimator 128. In one embodiment, processor 102 stores in memory 106 a record of whether the suggested bolus amount from the bolus estimator 128 was accepted or changed by the user, and records the suggested and changed bolus amounts. The stored data can be used for later analysis by downloading the data to a computer by wired, RF or IR transmissions, for example by IR transmissions from the external infusion device 100 through a communication station to the computer, or the like as previously described.

Some embodiments of the invention employ a normal bolus. In alternative embodiments, the user may be given the choice of a normal, dual, square wave bolus, extended bolus, profiled bolus, or the like, by enabling these capabilities on the variable bolus menu in the setup menu on the external infusion device 100. If the variable bolus capability is not enabled, then every bolus would be a normal bolus. Preferred embodiments of the present invention use normal one-time boluses. However, alternative embodiments may utilize different bolus types to spread out the correction or meal bolus determined by the bolus estimator 128.

Since the external infusion device 100 stores the time of each bolus delivery, simple algorithms as illustrated above can be designed to take into account the amount of insulin that might still be remaining in the user's body from a previous bolus. The longer the programmed time for the "Insulin Duration Factor" then the more conservative the estimate becomes. In other embodiments, the external infusion device 100 can adjust for several boluses that were delivered within the insulin duration window. Although it is difficult to absolutely predict how long insulin will actually remain active in the body, the above-described algorithm does at least consider the effects on the amount of insulin actually needed. This provides an additional level of conservative estimation in the external infusion device 100 by accounting for insulin delivered within a programmable window. Without such an algorithm, the infusion device 100 could suggest a larger bolus than required because the remaining insulin might not have been accounted for in the suggested bolus.

The bolus estimator 128 has the advantage of prompting the user to enter his/her blood glucose (BG) value, and thus also serves as a useful reminder to check BG levels regularly. This makes testing more advantageous, since the results directly assist the user in maintaining control of the patient's condition. Also, the bolus estimator 128 enables the external infusion device 100 to capture information on carbohydrate intake which is valuable for helping the user to refine carbohydrate counting skills. This data may also be downloaded to a PC, laptop, communication station, RF programmer, or the like and applied to programs to provide an advanced analysis of the patient's insulin needs.

In other embodiments, an external infusion device 100 and user can utilize the bolus estimator 128 information to "learn" insulin sensitivity values, carbohydrate counting, the effects of high fat meals and other variables that can lead to better control, and use this to adjust the results of the bolus estimator 128. In alternative embodiments, the user can omit entering specific carbohydrate amounts each time calculations are made by the user. For example, the external infusion device 100 may store the carbohydrate amounts for several meals that are regularly eaten by the user in the memory 106, and then allow the user to recall the stored meals. In other alternative embodiments, a list of general foods to may be provided with a carbohydrate equivalent. In other embodiments, the external infusion device 100 may utilize a more complicated keypad and/or RF programmer 110, and a code can be assigned for each food. Then the code for each food to be consumed can be entered into the external infusion device 100.

Figure 3A:
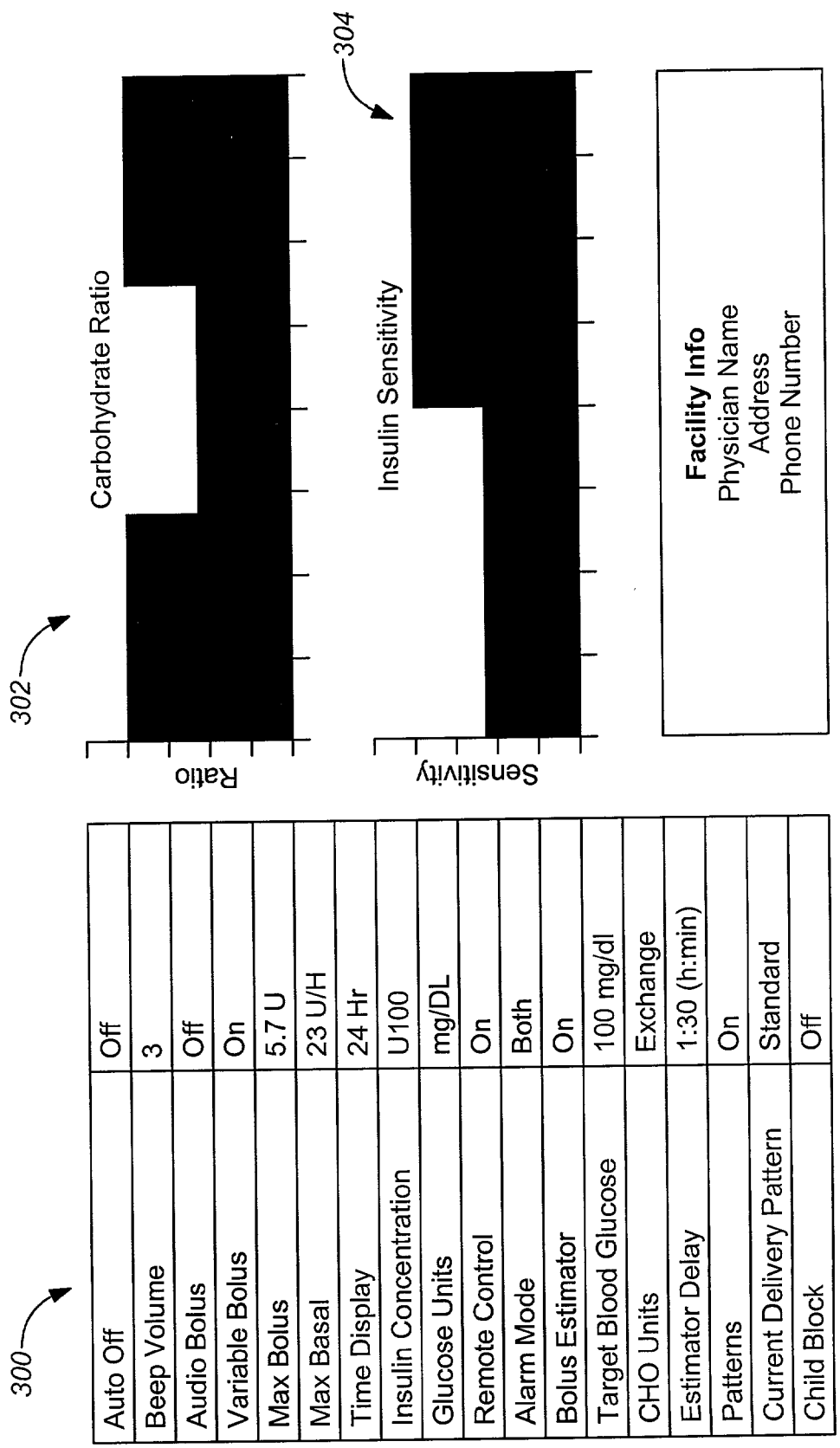
FIG. 3A illustrates fixed and variable settings of the bolus estimator.

FIG. 3A illustrates how the settings 300 of the bolus estimator 128 may be fixed or variable. One or more of these settings (e.g., the carbohydrate ratio, target blood glucose and insulin sensitivity), can follow a profile that changes over the course of a day. FIG. 3A shows example profiles for the carbohydrate ratio 302 and insulin sensitivity 304 values that vary over a daily schedule. Using these profiles enables the bolus estimator 128 to provide a more accurate estimate of the appropriate amount of insulin for a patient at a given moment. Different profiles can also be used for different days. In general, profiles can be generated to account for the anticipated activities of the patient which affect the medication needs of the patient. For example, a workday profile may be different than a weekend day profile. Days during which the patient plans to exercise can have a different profile than days spent at rest. In addition profiles can also be created for different lengths of time. For example, a weeklong profile can be created around a patient's default routine. Short duration profiles to accommodate unplanned activities can then be inserted as necessary.

The bolus estimator 128 can store values of current BG, carbohydrates to be consumed and the estimated and actual bolus size and type which can be used to provide valuable information to the user. This data of the bolus estimator 128 can be used to develop an understanding of how time of day and other global effects should be accounted for in using the estimator 128. For example, the data can be used to calculate improved values for the carbohydrate ratio and the insulin sensitivity. The data accumulated by the estimator includes a record of insulin delivery as well as blood glucose measurements.

Figure 3D:
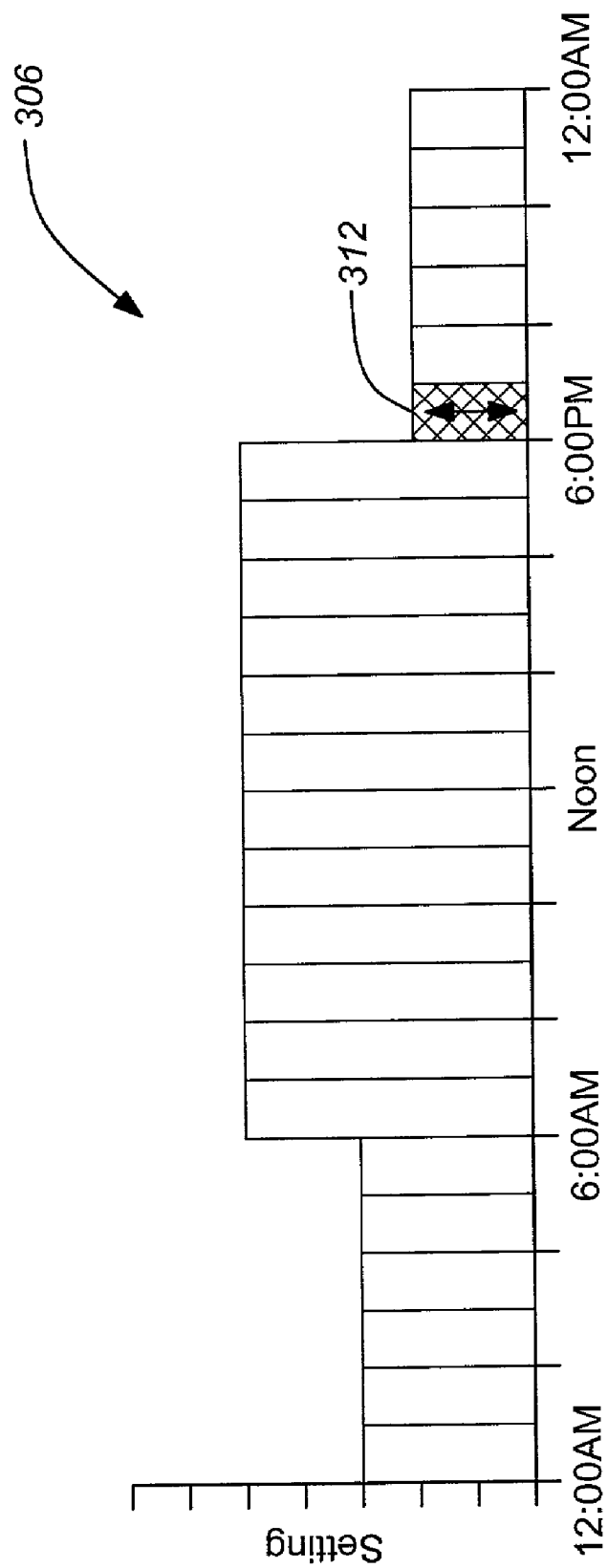

FIGS. 3B–3D illustrate a graphical programming interface for setting profiles. In some embodiments of the invention, profiles can be set using a convenient and efficient graphical interface. Using the interface a profile description 306 is shown in graphical form. The description 306 is composed of a series of discrete setting divisions for the particular parameter being programmed. The user begins by moving an indicator (e.g., a flashing division) from one end of the profile description 306 until he arrives at the first division 308 in the profile that he wishes to modify. At this division, the user indicates (e.g., using an up and down arrow selector) the desired value for the particular first division 308. In response, the interface automatically applies an identical value to the subsequent division in the profile description 306. In other words, each following division is set at the same level as the adjusted division. See FIG. 3B. Following this the user begins to move the indicator to the next division 310 that he wishes to adjust from the setting of the first division 308. All intervening divisions will retain the setting of the first division 308. See FIG. 3B. This division 310 is now adjusted and again all subsequent divisions are adjusted to match. Prior divisions in the profile, however, remain unchanged from the setting of the first division 308. As shown in FIG. 3D, the process can be repeated by moving the indicator onward and setting subsequent divisions (e.g., division 312). Because the user is not required to enter a setting for every division in the profile description, the graphical interface enables a user to quickly enter a desired profile without tedious and repetitive effort. In addition the graphical interface can also display the time, setting value or rate and total for the programmed profile. It should be noted that this graphical interface can be used for setting any parameter that uses a profile (e.g., carbohydrate ratio, insulin sensitivity as well as bolus profiles which will be detailed hereafter).

Figure 4:
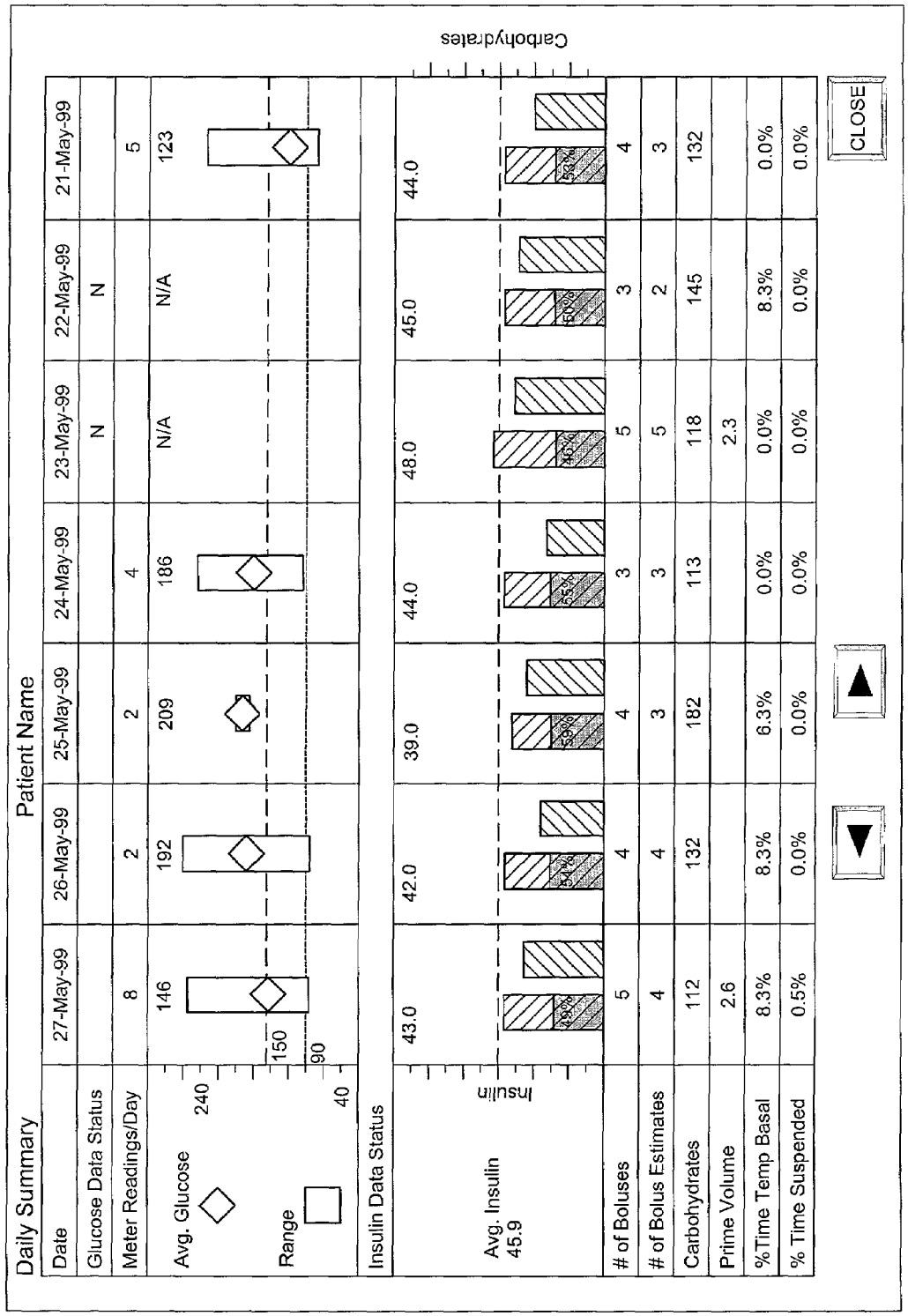
FIG. 4 illustrates daily summaries of carbohydrate and insulin intake.
Figure 5:
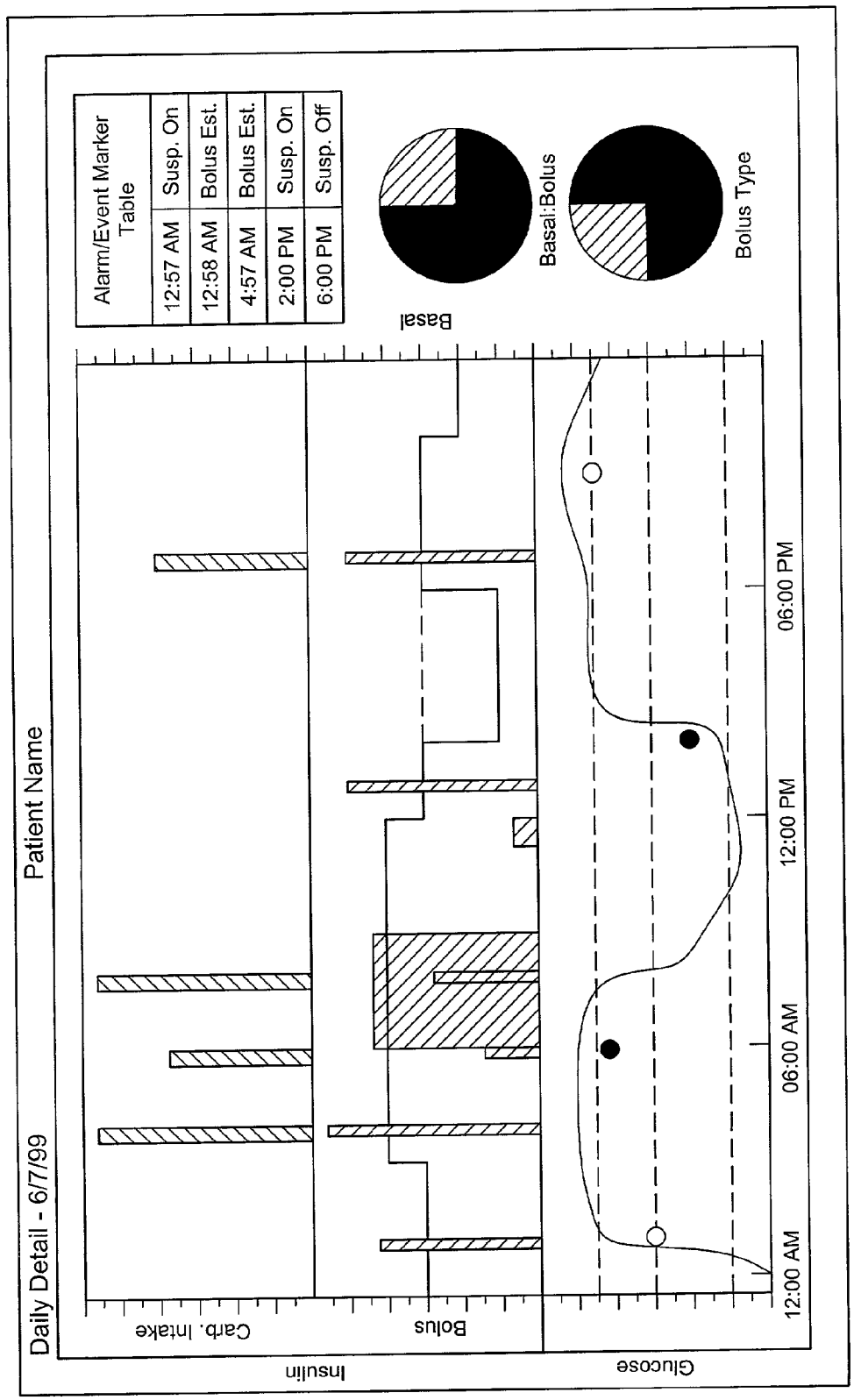
FIG. 5 illustrates detailed carbohydrate, glucose and insulin information for a single day.

FIGS. 4 and 5 illustrate, respectively, exemplary daily detail and summary screens for bolus estimator use and carbohydrate intake in an analysis program. FIG. 4 illustrates daily summaries of carbohydrate and medication intake. FIG. 5 illustrates detailed carbohydrate, glucose and insulin information for a single day. Use of the bolus estimator can also be tracked in the detail and summary screens. This information can be used to monitor patient use of the bolus estimator as well as improve the accuracy of the bolus estimator function.

FIG. 4 illustrates a daily summary report screen. This report provides a summary of information relating to the glucose data status and insulin data status for a particular day. Alternatively, it may provide a report for several days in a summary format as shown. The glucose data status section shows the number of readings, the average glucose value and the range. The insulin data status section shows total amount of insulin taken, the number of boluses, the number of bolus estimates, the carbohydrate use, the prime volume, the percent of the time that a temporary basal rate was used, and the percent of time that the infusion pump operation was suspended.

FIG. 5 illustrates a daily detail report screen. This report provides a detailed daily view of infusion pump, glucose meter, and sensor (e.g., monitor) data. Each screen represents a single day's data and includes the following components: infusion pump data (e.g., insulin usage data), sensor and meter data (e.g., glucose data), alarm/event/marker table (e.g., including carbohydrate intake events) and pie charts (basal:bolus ratio and bolus type).

Carbohydrate intake is graphically shown in the upper section and indicates when and how much carbohydrate consumption has occurred. The graph is derived from carbohydrate consumption events (such as indicated by meal or snack markers) from the event marker table that have been logged by the user. The event markers can be logged into the pump and stored for later downloading or entered directly into the running software program. The exemplary event marker table is shown in the upper side section of the report screen and is further detailed below.

The infusion pump data is shown in the middle section and graphically depicts basal rate, bolus, prime, and alarm history for the specified day. The basal rate is shown as a line indicating: normal basal rate, temporary basal rate, auto-off, and suspend (e.g., the programmed normal basal rate can be shown as a dashed line during any of: suspend, temporary basal rate, or auto-off). Boluses delivered can also be indicated. The alarm markers will be positioned to show the time of any alarm. In the illustrated report, two insulin scales are marked due to the relative scale of a bolus (large) compared to a basal rate (small). The bolus scale shall be on the left y-axis and the basal scale shall be on the right hand y-axis. In particular embodiments, any priming events will also be shown. Pie chart data is shown in a lower side section and graphically depicts basal:bolus ratio and bolus type as pie charts.

The sensor and meter data is shown in the lower section and graphically depicts meter readings and sensor data-vs.-time for the specified day. Any continuous glucose monitor (i.e., sensor) readings can be displayed as a continuous line graph. Meter readings can be marked as either a reference value or as calibration points. Any sensor event markers, such as small rectangular markers, or the like, at the bottom edge shall depict sensor event markers.

The alarm/event/marker table is shown in an upper side section and will be shown only if either infusion pump, glucose meter, glucose monitor (i.e., sensor) or carbohydrate consumption data are present. Alarms and events from the infusion pump, glucose meter and glucose monitor can be listed in order of time of the event/alarm. Textual definitions for events shall be listed if defined; otherwise a numeric value for the events shall be shown. For example, the table can display the following events involving programming changes for the current day: Time/Date change—displays new date (in mm-dd-yy format) and new time, where the time change is displayed in either 12 or 24 hr format depending on user's settings; Suspend On/Off—time the feature was turned on and was time turned off; Temporary basal rate—displays setting of a Temporary Basal Rate including amount in units per hour (e.g. 0.6 u/h) and duration displayed in same format as duration for bolus history; Basal Rate change—a note referring to a Basal Profile section for basal rate change history; battery removal/replacement—displays the removal and subsequent replacement of batteries with time of action; Maximum Basal Rate change—changes of the setting along with the time of action; Maximum Bolus change—displays the change of setting along with the time of action; Insulin Concentration change—displays the change of concentration; Auto Off Change—displays new feature setting along with the time of change displayed in hours; Alarm/Error Code—brief description of the alarm/error.

Furthermore, a variety of additional event markers can be stored in the event log in the memory 106 of the infusion pump. Markers can identify any significant events (beyond mere programming changes) which relate to the administration of medication to a particular patient and can be useful in improving dosage estimating. For example, a meal marker can identify a significant carbohydrate intake and a snack marker can identify a less significant intake. Any range of markers indicating a range of carbohydrate intake values can be used. Markers can also be used to indicate low or high BG values. Exercise, illness and stress, which also affect appropriate medication dosage, can also be tracked with event markers. At least some of these events can be taken as inputs to the bolus estimator 128 in calculating an insulin dosage. In this way the bolus estimator can provide a complex analysis of insulin need in real-time for the patient based upon the most current readings an estimates of BG values. For example, the infusion device 100 can track BG values and insulin use along with the number of hypo- and hyper-medication readings, as well as the patient response to high or low BG. In addition, the event log can be downloaded to be used in other analysis software to identify broader trends which can be used to improve the bolus estimator 128 predicative abilities for a particular patient. Thus, event markers can be used in conjunction with the pump memory (e.g., the memory of the bolus estimator 128) and glucose data (e.g., from a glucose sensor and meter) to provide specific and average pre- and post-event analysis. Embodiments of the present invention provide a convenient way to accumulate accurate event data by capturing the information directly in the pump.

Similar to the setting profiles (e.g., carbohydrate ratio and insulin sensitivity), medication can be delivered through the infusion device according various profiles which vary over time. For example a basal profile represent a base level of insulin which is delivered over a period of time. Various bolus profiles can also be used in response to more immediate needs of the patient, such as from eating a meal. Some examples of bolus profiles include a square wave and a dual wave profile. The infusion device can be programmed to deliver insulin according to various profiles. Details of the operation of an exemplary infusion device are provided in U.S. patent application Ser. No. 09/334,858, filed Jun. 16, 1999, which is incorporated by reference herein.

Although dual wave bolus delivery provides a good match to a user's need, the number of operations required to employ the dual bolus (as well as other advanced infusion device operations) may limit it use by some patients. To address this, embodiments of the present invention employs simplified dual wave bolus programming. Dual wave bolus programming is activated through a menu presented to the user.

In one embodiment of the invention, the user enters the total desired insulin volume and that volume is divided into the two portions of the dual wave bolus, the immediate and the delayed portions, by a predefined ratio. The ratio may be fixed as a preselected setting or adjustable as a user setting. In a further embodiment, the delay time between the immediate and delayed portions is also predefined by a user setting. For example, a delay of 1½ hours can be defined at the factory.

In another embodiment, the delivery bolus profile (e.g., dual wave, square or other) can be set such that one form can be used by default. This eliminates the need for the user to specify the bolus profile every time.

In yet another embodiment, the user can select the level of programmability with respect to the dual wave bolus. A setting of full programmability can allow/require the user to program all aspects of the dual wave bolus per a traditional menu as initially described. A setting of a lower level of programmability can require some values to be input directly (e.g. the ratio between the immediate and delayed portions) while other values (e.g. the delay time) are taken from stored values. The lowest level of programmability merely requires entry of the total desired insulin volume; other required values are taken from stored preselected settings. Thus, with only one entry, a dual bolus can be delivered.

It should be understood that although simplified bolus programming is described here with respect to programming a dual wave bolus, simplified bolus programming can be applied to any bolus profile including square wave bolus profiles.

3. Convenience Features

Other embodiments of the invention can employ a suspend function which automatically delivers a "take a break bolus" to allow a patient to disconnect from the infusion device 100 for a predetermined period. This function is particularly well adapted for short acting medications. The purpose of this capability is to deliver an extra bolus before disconnecting from the external infusion device 100 to make certain that the needed amount of medication is delivered before interrupting the administration. This can help the user remain above the minimum therapeutic level during an interruption of medication delivery. Preferably, four durations of an interruption of the medication infusion are used: 30 minutes; 1 hour; 1 hour and 30 minutes; and 2 hours. However, additional, or longer or shorter intervals may be used. Generally, this capability is activated in the setup menu by the health care specialist, who can program the dose for each of the possible times of delivery interruptions. The dose is set based on the medication and the condition of the user. If the health care specialist programs only certain durations (for example, 30 minutes and 1 hour only), the user will only be able to take a break for those durations. In alternate embodiments, the user can set the break duration and associated dosages. In preferred embodiments, in the "take a break bolus" menu screen, the user can program the duration of the planned interruption. The external infusion device 100 can then beep after the delivery of the previously set dose. The user can then disconnect from the external infusion device 100 and can be reminded by the external infusion device 100 to reconnect when the time is up. Preferably, the reminder alarm can continue to sound (or vibrate) until the user reactivates the external infusion device 100. In alternate embodiments, the infusion device has a dedicated button, touch-screen button or other method, for the user to activate a "take a break" bolus.

Figure 6:
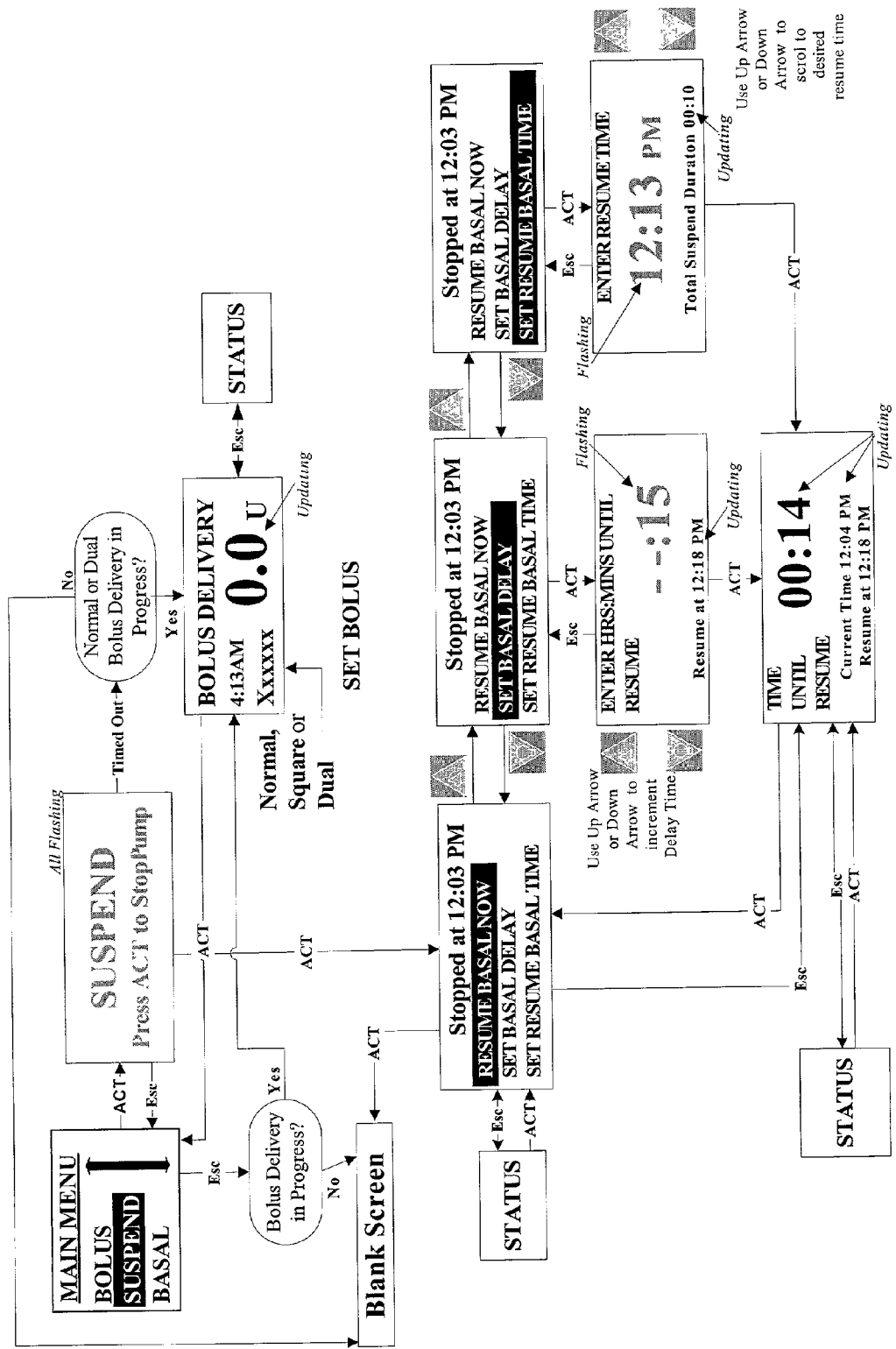
FIG. 6 is a flowchart illustrating a suspend function embodiment of the invention.

Other embodiments of the invention can use a more versatile suspend function. For example, FIG. 6 is a flowchart illustrating a suspend function embodiment of the invention. Upon selecting the suspend function, the user is presented with a menu to select the period for suspension. In one embodiment, predetermined intervals (e.g., ½ hour, 1 hour, 2 hours, etc.) are presented to be selected as described above. In another embodiment, as illustrated in FIG. 6, the suspend duration can be incremented by a predetermined amount (e.g., 15 minute or 30 minute intervals under the "SET BASAL DELAY" menu) and then entered. Also as illustrated in FIG. 6, in yet another embodiment, the user may specify a particular time (e.g., 12:13 PM under the "SET RESUME BASAL TIME" menu) for the pump to resume operation. The appropriate "take a break bolus" can be determined as a function of the selected time based upon settings provided in the setup menu.

The infusion device 100 also allows for selective suspension of specified functions. The infusion device can be programmed to deliver at a rate defined by a basal profile or in a bolus. A bolus can be delivered all at once and it can also be spread over a period, such as with the square wave or dual wave profiles. The delivery profiles can also be simultaneously programmed into the infusion device. In this case, when a user wishes to suspend operation of the infusion device, the user can be given the option of activating a complete suspension or selecting which profile(s) to suspend. For example, if the user has programmed the infusion device to deliver a bolus and then changes his mind, the user may want to immediately suspend the bolus (e.g., square or dual wave), but may want to maintain the basal delivery rate. In another example, the user may want to suspend delivery of the basal profile, but maintain delivery of a bolus profile.

In addition, when the user restarts the infusion device 100 after a suspended operation the user can select which profiles are to be resumed and how they shall be resumed. In one embodiment, the user can select to resume a suspended square wave or dual wave bolus to restart at the point it was suspended. In another embodiment, the user can select to restart the basal profile. In another embodiment, the user may also select that the restarting the infusion device includes calculation and delivery of a compensating bolus to account for the fluid missed as a result of the suspended operation.

It is also important that suspending the operation of the infusion device does not require multiple operations in an emergency. Therefore a dedicated button or key can be provided to directly cause full suspension of all pump delivery. The selective suspend functions previously discussed are accessed through a separate menu. A warning signal can be provided through the speaker if a suspend function is enabled to indicate the operation status to the user. In addition, the dedicated suspend key can call up the suspend menu for further selections by the user.

Embodiments of the present invention also allow the alarm volume to be programmed according to a profile. In one embodiment, the user can select different volume levels for different time periods of the day. For example, the user may select a low volume level from 8 AM to 10 PM and a high volume level from 10 PM to 8 AM. Of course, any number of periods and multiple volume levels can be used. This aspect of the invention enables users to have a desired alarm volume at a desired time without having to manually change the volume setting daily.

4. Safety Features

Embodiments of the present invention include a variety of safety features that assist in preventing misuse of the infusion device. Warnings, such as a screen displaying full circles, symbols, messages, color changes, flashing, a special font style, or other means used to get the user's attention, can be used to inform the user of a potentially unsafe condition. Such warnings can be used for conditions including, low battery voltage, an empty or low reservoir, excessive bolus requests, an unusually large bolus request and the like.

In addition, from time to time the user can temporarily remove the infusion device. It is important that the infusion device is not misplaced. Using the RF remote, embodiments of the present invention allow the user to readily identify the location of the infusion device by activating a transmitter in the remote and cause the infusion device, receiving the signal, to emit an audible signal through the speaker. Furthermore, the RF remote can be equipped with a speaker and, by the same principle, the infusion device can trigger the RF remote to issue an audible signal so that the user can quickly locate the RF remote. Using either of these "find functions" of the infusion device and RF remote pair, the user can quickly locate one device with the other.

In other embodiments a "lockout function" can be included to restrict operation of the infusion device 100. Preferred embodiments can have multiple lockout levels, with the selection dependent upon the anticipated usage, the external infusion device model, the sophistication of the user, or the like. For example, the following lockout levels can be used. A lockout level means that some of the features of the external infusion device may not be accessible to the patient (or user), but will be accessible to the health care professional or the parent of a child using the external infusion device 100. Access control can be managed by requiring a password or some other authentication method. A lockout level of "None"(0) can let the user program and access all features of the external infusion device 10. A lockout level of "Setup"(1) can generally lock the user out of changing the setup menu parameters. The user may only have access to activated features of the external infusion device 100, but can not change the pre-set parameters. The user will be able to review the settings, and only change the lockout level with an authorizing key sequence. The only setup feature that will still be available is selftest. A lockout level of "All except Suspend"(2) can only allow the user to suspend the external infusion device and to perform a selftest. All other features can be locked out. The user can be able to review the settings, and only change the lockout level with an authorized key sequence. Finally, the "Lockout function" can be accessed in the setup menu. A special key sequence (or code) can be required to change the lockout level. This can minimize the possibility of an unauthorized change of the lockout levels. In preferred embodiments, an icon (lock) can be displayed on the display 114 when the external infusion device 100 is in lockout mode 1 or in lockout mode 2.

Preferred embodiments of the external infusion device 100 can include a configurable menu that can be accessible by password through the use of a PC, laptop, RF programmer or the like. This ability allows the physician, or sophisticated user, to select only the external infusion device 100 capabilities that are required for an individual user. A "lock out" capability can enable the physician to exclude certain options from the user. This may be useful with new users or children using the external infusion device 100.

In another embodiment, a user can enable a block function that limits the operation of the infusion device. The block function can be employed in situations where the patient must be supervised in using the infusion device, such as when the patient is a child or very elderly and there is a risk that they will inadvertently misuse the infusion device and possibly harm themselves. Enabling the block function limits the maximum bolus delivery in some fashion. For example, in one embodiment, the maximum bolus dose and/or the maximum basal rate are limited. The block function can also be set to operate by a predetermined schedule. For example, the block function may operate during a period when operation of the infusion device will be regularly unsupervised, such as when a child is at school.

In preferred embodiments, there can be a maximum number of external infusion device 100 strokes for the drive mechanism 118 that may occur in one hour based on the maximum basal rate and bolus amounts. Typically, the external infusion device 100 can sound (and/or vibrate) and the external infusion device 100 will not be able to deliver more than ((2.5 * maximum bolus)+maximum basal+1) strokes in one hour. Preferably, the external infusion device 100 will deliver medication in 0.1 units volume increments (although other increments may be used). The actual amount of insulin or medication in a given stroke depends on the insulin or medication concentration, stroke length and delivery reservoir diameter or cross-sectional area. In preferred embodiments, the delivery rates are scrolled by the amount of insulin per stroke. The rate delivery pattern can be calculated by dividing the number of strokes required for the rate into 3600 (the number of seconds in one hour). The result is the number of seconds between each stroke. The rate can be delivered evenly over the hour, each stroke on a one-second boundary. Rates that do not divide evenly into 3600 will not have any accumulating error. For example, consider a rate of 3.0 units per hour and a concentration of U-100 3.0 U/hr at U-100 will require 30 strokes per hour. This translates to a pump stroke every 3600/30=120 seconds, or one stroke every two minutes. In alternative embodiments, the drive mechanism 118 may provide for continuous flow rather than incremental or pulsed flow rates. Further alternatives may omit strokes and utilize hydraulics, pneumatics, step motors, continuous motors, or the like.

The suspend and/or block functions can be triggered by monitoring the amount of infused medication. The amount of infused medication can be determined by integrating the pump rate over a period of time. The pump rate can be measured by the active delivery profiles (basal, square wave bolus, dual wave bolus, etc.). The monitored period (e.g., at one hour intervals) continuously repeats itself, comparing the accumulated total to a target limit derived from a maximum basal and maximum bolus limit.

In one embodiment of the invention, more than one integration can be simultaneously performed at staggered and overlapping intervals. Without such multiple integration operations, a potentially harmful amount of medication could still be delivered if its delivery spans two integration periods.

Figure 7A:
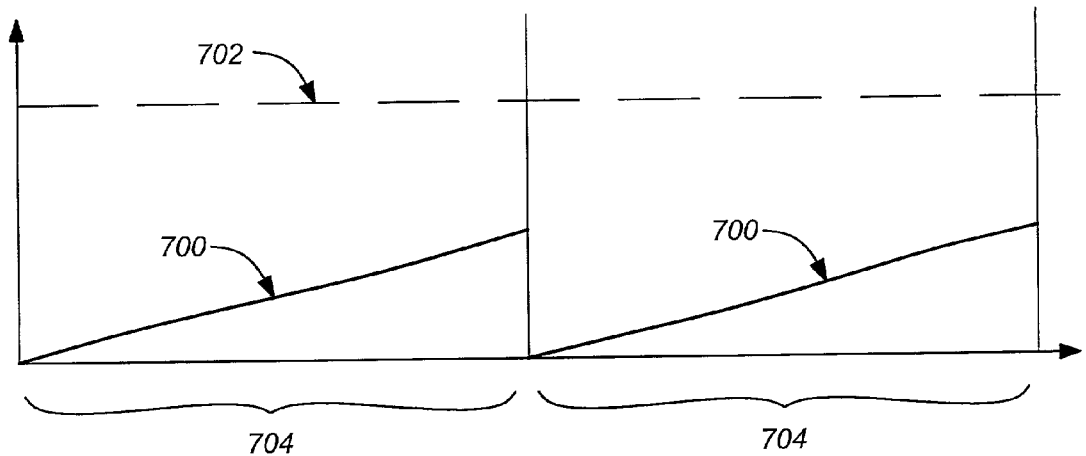
FIGS. 7A–7C illustrate integration plots for triggering the block function.
Figure 7B:
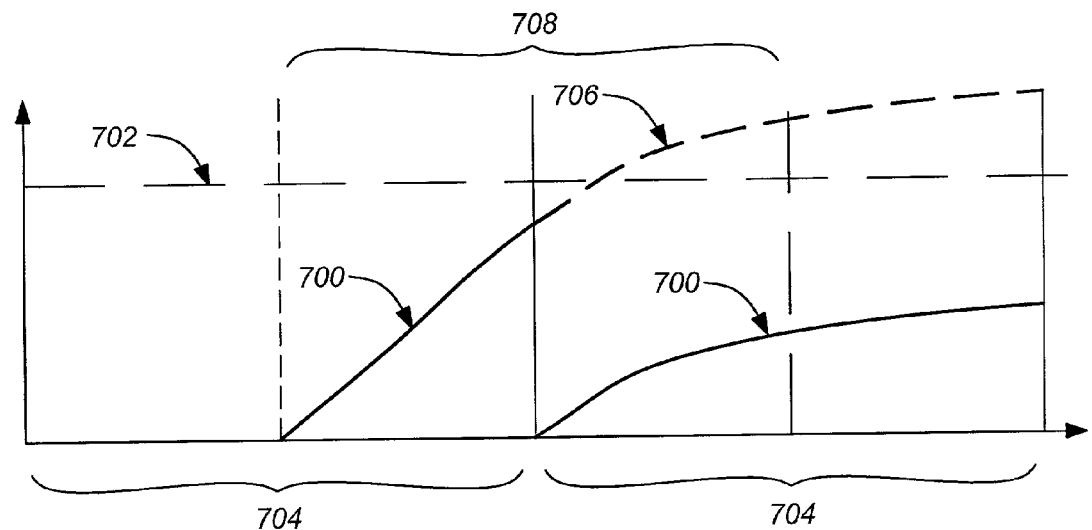
Figure 7C:
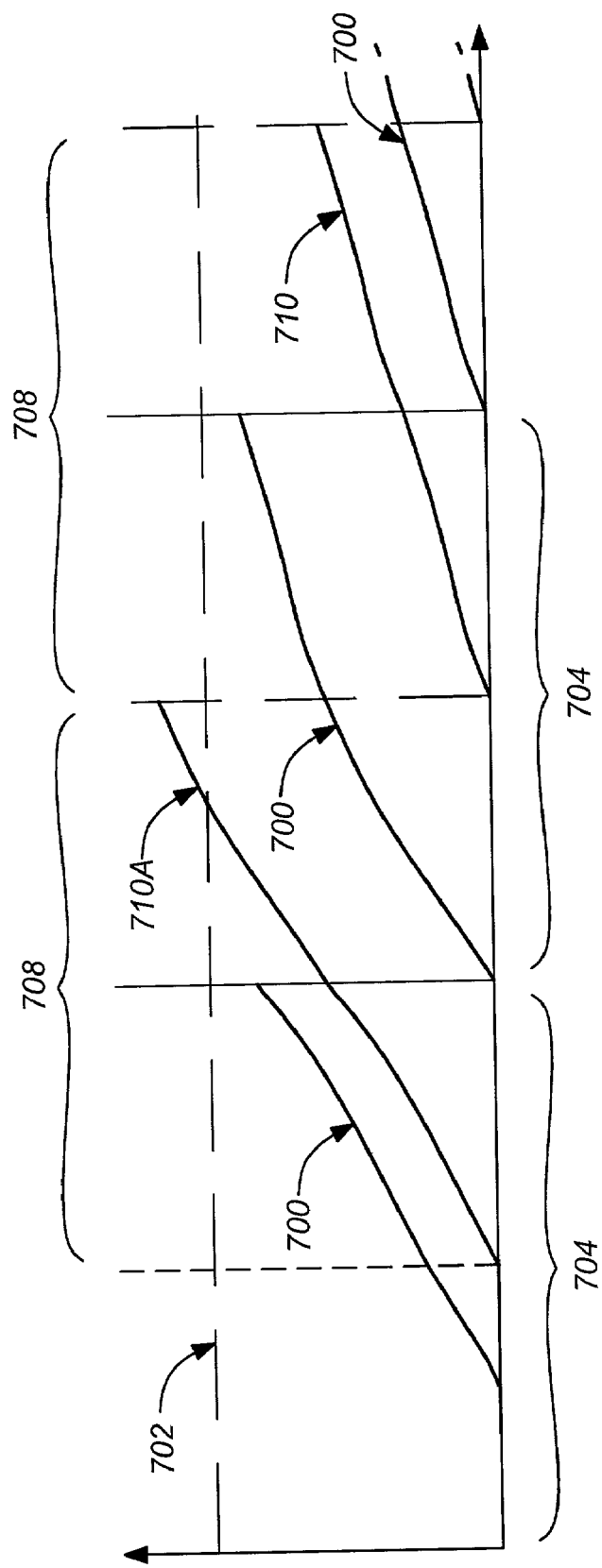

FIGS. 7A–7C illustrate integration plots for triggering the block function. FIG. 7A illustrates the integration plot 700 of the infusion rate that repeats after a fixed period. If a preselected target level (e.g., a specific over-infusion amount of insulin based on a maximum bolus and maximum basal rate) 702 is exceeded within any single period 704, the block function can be enabled. FIG. 7B illustrates integration plots 700 where the target level 702 is not exceeded in the first or the second period because the integration is restarted at the beginning of the second period. It can be seen from the extended line 706 that the target level would have been exceeded if medication delivery had been integrated over an alternate single period 708. FIG. 7C illustrates two repeating staggered and overlapping integration plots 700, 710. The two plots are integrated over equivalent periods 704, 708 that are out of phase with each other. For example, the periods can be 1-hour long and 30 minutes out of phase with each other. A potentially harmful dose, which would have escaped detection using only the first integration plot 700, is now detected by the second overlapping integration plot 710.

It should be understood that staggered and overlapping integration periods are equivalently implemented by shortening the integration period and storing the final total from the previous integration period. The stored value can be added to the current integration and the total can be checked against the target. This is true because two simultaneous integration plots produce the same change in their respective medication totals. In effect, embodiments of the invention can divide the full monitored period into two integration subperiods The full monitored period can be subdivided into multiple integration subperiods, each concluding with a final subtotal representing the medication delivered over each subperiod. The system stores the final subtotals of the multiple integration periods. As each new integration period is concluded, the new total replaces the value of the oldest stored subperiod.

The optimum number of subperiods (i.e. the subperiod size) to use can be determined by proposing a hypothetical subperiod size and determining the total amount of medication that could possibly be delivered by the infusion device during the hypothetical period (based upon the maximum delivery capacity of the infusion device, for instance). If this amount can be acceptably ignored as it is replaced as the oldest subtotal, the subperiod size is acceptably small.

In addition, embodiments of the invention can also improve performance of block function triggering by synchronizing the integration periods with infusion device operation. For example, the pump may ignore any period of negligible infusion prior to beginning a significant medication infusion. The integration period can be initiated when a sudden change in infusion is detected. In this way, monitoring for the block function can be appropriately synchronized with higher infusion rates.

In another embodiment of the invention, the target level is based upon an analysis of actual infusion device use for a given patient that is incorporated into the infusion device. This dynamic target level can, for example, be based upon a historic daily average (e.g. over a week or 10 days) of the maximum count of infused medication for an integration period for each day. An appropriate margin can be added to the historic daily average to obtain the dynamic target level from the historic daily average. In such embodiments of the invention, the infusion device stores values of the maximum count of medication delivered in an integration period of each day. If, in a given integration period, a total amount of an infused medication exceeds the dynamic target level, the suspend and/or block functions can be invoked. This dynamic target level and associated monitoring provides the benefit of tracking changes in infusion use over time. For example, a weight change of the patient that causes a gradual increase or decrease in insulin use can gradually alter the dynamic target level.

In preferred embodiments of the invention, this dynamic target level is used instead of a typical fixed target level (e.g. one based strictly upon a fixed maximum bolus and/or maximum basal infusion rate). In specific embodiments of the invention, the user can select between a dynamic target level and a fixed target level. For example, in contexts where a sufficient number of days of history have not yet accumulated so as to yield a meaningful daily average, the dynamic target level can be superceded (even if selected) in favor of a fixed target level until a such history is established.

The historic daily average, upon which the dynamic target level is based, can be maintained in the infusion device memory and adjusted at the conclusion of each day by formulae such as the following:

$$T_i = \frac{T_{i-1}(N-1) + G}{N}$$

where, $T_i$ is the new daily average, $T_{i-1}$ is the previous daily average, N is the number of days of historic use and G is the new maximum medication count. An appropriate margin (e.g., up to 3 standard deviations or a percentage of the daily average) is added to the new daily average to determine the new dynamic target level. For example, the new dynamic target level can be simply set at 20% over the daily average. Alternately, embodiments of the invention can calculate a standard deviation value from the historic use to determine an appropriate margin to add to the new daily average and determine the new dynamic target level. For example, the new target level can be the new daily average plus three standard deviations.

As can be observed from the equation above, the number of days of historic use of the medication delivery system (N) influences the determination of the dynamic target level. In this context, the selection of N influences the responsiveness of the dynamic target level to more recent changes in infusion use. An average level from a fewer number of days produces a dynamic target level that changes quickly in response to recent use. In contrast, as the number of days of historic use is increased, the dynamic target level is more stable and less affected by possibly anomalous recent fluctuations in medication use. In such situations, a balance can be struck between the desired responsiveness of the delivery device and stability in the selection of the appropriate number of days of historic use. In addition, calculating a new dynamic target level the invention can disregard medication counts for days during which a previous dynamic target level was exceeded.

The foregoing description including the preferred embodiments of the invention has been presented for the purposes of illustration and description. It is not intended to be exhaustive or to limit the invention to the precise form disclosed. Many equivalent modifications and variations are possible in light of the above teaching.

It is intended that the scope of the invention be limited not by this detailed description, but rather by the claims appended hereto. The above specification, examples and information provide a complete description of the manufacture and use of the apparatus and method of the invention. Since many embodiments of the invention can be made without departing from the scope of the invention, the invention resides in the claims hereinafter appended. Throughout the specification various patents and other references are cited. The disclosures of these are incorporated by reference in their entirety.

What is claimed is:

1. A system for delivering medication, comprising:
   an infusion pump coupleable to a medication reservoir; and
   a control system having an algorithm for controlling medication delivery by the infusion pump;
   wherein the control system includes:
   a plurality of medication delivery profiles for delivering a medication from the medication reservoir to a user including a basal profile and a square wave bolus profile or a dual wave bolus profile; and
   a plurality of suspend functions capable of separately suspending at least one of the plurality of medication delivery profiles so that a user can suspend a first delivery profile that delivers a medication from the medication reservoir to a user while a second delivery profile continues to deliver the medication from the medication reservoir to the user.

2. The system of claim 1, wherein controlling medication delivery by the pump includes using two or more wave profiles and wherein the control system includes a suspend function for separately suspending each of the two or more wave profiles.

3. The system of claim 2, wherein the control system further includes a resume function for selectively restarting each of the more than one wave profile.

4. The system of claim 2, wherein the control system further includes a compensating function for delivering a compensating bolus to account for any suspended wave profile.

5. The system of claim 2, wherein the suspend function further includes a full suspend function for directly suspending all delivery of medication.

6. The system of claim 2, wherein the more than one wave profiles are selected from the group including a square wave bolus profile, a dual wave bolus profile and a basal profile.

7. The system of claim 1, wherein the suspend function includes a menu system for selecting a period of time for temporarily suspending medication delivery by the infusion pump.

8. The system of claim 7, wherein the menu system includes a plurality of fixed periods from which to select as the period of time for temporarily suspending medication delivery.

9. The system of claim 7, wherein the menu system includes one or more increment periods increment the period of time for temporarily suspending medication delivery.

10. The system of claim 7, wherein the menu system includes a specified time of day to select as an end of the period of time for temporarily suspending medication delivery.

11. The system of claim 7, wherein after the period of time for temporarily suspending medication delivery by the infusion pump has transpired the pump resumes medication delivery.

12. The system of claim 1, wherein the suspend function includes a block function for suspending delivery of medication after a potentially harmful amount of medication requested by a user and a warning to the user of the potentially harmful amount of medication.

13. The system of claim 12, wherein the potentially harmfully amount of medication is bolus.

14. The system of claim 12, wherein the potentially harmfully amount of medication is a bolus requested too soon after a previous bolus is delivered.

15. The system of claim 12, wherein the potentially harmfully amount of medication is too low a total medication dose for the day.

16. The system of claim 12, wherein the block function is triggered after a medication measurement integrated over an integration period exceeds a target value.

17. The system of claim 16, wherein the block function is alternately triggered because a second medication measurement integrated over a simultaneous and overlapping integration period exceeds the target value.

18. The system of claim 16, wherein the integration period is subdivided into a plurality of subperiods and each of the plurality of subperiods is associated with a subtotal representing medication delivered and an oldest subtotal of the subperiods is replaced by a newest subtotal of the subperiods.

19. A method of delivering medication, comprising:
   controlling medication delivery by an infusion pump coupled to a medication reservoir, wherein the infusion pump includes a control system comprising an algorithm, and wherein the control system includes a plurality of medication delivery profiles including a basal profile and a square wave bolus profile or a dual wave bolus profile and a plurality of suspend functions capable of separately suspending the plurality of medication delivery profiles so that a user can suspend a first delivery profile that delivers a medication from the medication reservoir to a user while a second delivery profile continues to deliver the medication from the medication reservoir to the user; and temporarily suspending a medication delivery profile from the infusion pump with a suspend function of the control system.

20. The method of claim 19, wherein the step of controlling medication delivery by the pump includes using two or more wave profiles and wherein the control system includes a suspend function for separately suspending each of the two or more wave profiles.

21. The method of claim 20, further including selectively restarting each of the more than one wave profile with a resume function of the control system.

22. The method of claim 20, further including delivering a compensating bolus to account for any suspended wave profile with a compensating function of the control system.

23. The method of claim 20, wherein the suspend function further includes a full suspend function for directly suspending all medication delivery.

24. The method of claim 20, wherein the more than one wave profiles are selected from the group including a square wave bolus profile, a dual wave bolus profile and a basal profile.

25. The method of claim 19, wherein the suspend function includes a menu system for selecting a period of time for temporarily suspending medication delivery by the infusion pump.

26. The method of claim 25, wherein the menu system includes a plurality of fixed periods from which to select as the period of time for temporarily suspending medication delivery.

27. The method of claim 25, wherein the menu system includes one or more increment periods increment the period of time for temporarily suspending medication delivery.

28. The method of claim 25, wherein the menu system includes a specified time of day to select as an end of the period of time for temporarily suspending medication delivery.

29. The method of claim 25, wherein after the period of time for temporarily suspending medication delivery by the infusion pump has transpired the pump resumes medication delivery.

30. The method of claim 19, wherein the step of temporarily suspending includes suspending delivery of medication with a block function of the control system after a potentially harmful amount of medication is requested by a user and a warning to the user of the potentially harmful amount of medication.

31. The method of claim 30, wherein the potentially harmfully amount of medication is bolus.

32. The method of claim 30, wherein the potentially harmfully amount of medication is a bolus requested too soon after a previous bolus is delivered.

33. The method of claim 30, wherein the potentially harmfully amount of medication is too low a total medication dose for the day.

34. The method of claim 30, wherein the block function is triggered after a medication measurement integrated over an integration period exceeds a target value.

35. The method of claim 34, wherein the block function is alternately triggered because a second medication measurement integrated over a simultaneous and overlapping integration period exceeds the target value.

36. The method of claim 34, wherein the integration period is subdivided into a plurality of subperiods and each of the plurality of subperiods is associated with a subtotal representing medication delivered and an oldest subtotal of the subperiods is replaced by a newest subtotal of the subperiods.

37. The system of claim 1, wherein the infusion pump includes a reservoir for containing the medication, a drive mechanism to deliver the medication from the reservoir, a processor to control the control system, a memory to store the plurality of medication delivery profiles, an input device to allow a patient to command the infusion pump and a housing that houses at least a portion of the reservoir, at least a portion of the drive mechanism, the processor, the memory and at least a portion of the input device, wherein the control system controls medication delivery from the reservoir in accordance with the plurality of medication delivery profiles, such that two or more of the plurality of medication delivery profiles can be used to deliver medication at the same time.

38. The system of claim 37, wherein at least one of the plurality of suspend functions may be used independently of at least one of the other of the plurality of suspend functions, such that medication delivery continues from the reservoir in accordance with at least one of the plurality of medication delivery profiles.

39. The system of claim 1, wherein the infusion pump includes a reservoir for containing the medication, a drive mechanism to deliver the medication from the reservoir, a processor to control the control system, a memory to store the plurality of medication delivery profiles, an input device to allow a patient to command the infusion pump and a housing that houses at least a portion of the reservoir, at least a portion of the drive mechanism, the processor, the memory and at least a portion of the input device, wherein the control system controls medication delivery from the reservoir in accordance with the plurality of medication delivery profiles, such that two or more of the plurality of medication delivery profiles can be used to deliver medication at the same time, and wherein at least one of the plurality of suspend functions may be used independently of at least one of the other of the plurality of suspend functions, such that medication delivery continues from the reservoir in accordance with at least one of the plurality of medication delivery profiles.

40. The method of claim 19, wherein the infusion pump includes a reservoir for containing the medication, a drive mechanism to deliver the medication from the reservoir, a processor to control the control system, a memory to store the plurality of medication delivery profiles, an input device to allow a patient to command the infusion pump and a housing that houses at least a portion of the reservoir, at least a portion of the drive mechanism, the processor, the memory and at least a portion of the input device, wherein the control system controls medication delivery from the reservoir in accordance with the plurality of medication delivery profiles, such that two or more of the plurality of medication delivery profiles can be used to deliver medication at the same time.

41. The method of claim 40, wherein at least one of the plurality of suspend functions may be used independently of at least one of the other of the plurality of suspend functions, such that medication delivery continues from the reservoir in accordance with at least one of the plurality of medication delivery profiles.

42. The method of claim 19, wherein the infusion pump includes a reservoir for containing the medication, a drive mechanism to deliver the medication from the reservoir, a processor to control the control system, a memory to store the plurality of medication delivery profiles, an input device to allow a patient to command the infusion pump and a housing that houses at least a portion of the reservoir, at least a portion of the drive mechanism, the processor, the memory and at least a portion of the input device, wherein the control system controls medication delivery from the reservoir in accordance with the plurality of medication delivery profiles, such that two or more of the plurality of medication delivery profiles can be used to deliver medication at the same time, and wherein at least one of the plurality of suspend functions may be used independently of at least one of the other of the plurality of suspend functions, such that medication delivery continues from the reservoir in accordance with at least one of the plurality of medication delivery profiles.

43. An infusion device for delivering a fluid from a reservoir to the body of a patient, the infusion device comprising:
  a drive mechanism to deliver the fluid from the reservoir to the body of the patient;
  a processor including a control system for controlling delivery of the fluid;
  a memory to store two or more medication delivery profiles associated with the reservoir;
  an input device to allow the patient to command the processor; and
  a housing that houses at least a portion of the reservoir, at least a portion of the drive mechanism, the processor, the memory and at least a portion of the input device;
  wherein the control system controls fluid delivery from the reservoir in accordance with the two or more medication delivery profiles, such that the two or more medication delivery profiles can be used to deliver fluid at the same time,
  wherein the control system includes at least two suspend functions capable of separately suspending at least one of the two or more medication delivery profiles, such that fluid delivery continues in accordance with at least one of the two or more medication delivery profiles, wherein each of the at least two suspend functions may be used independently of the other of the at least two suspend functions so that a user can suspend a first delivery profile that delivers a fluid from the reservoir to a user while a second delivery profile continues to deliver the fluid from the reservoir to the user.

44. The infusion device of claim 43, wherein the control system further includes a resume function for selectively restarting each of the two or more medication delivery profiles.

45. The infusion device of claim 43, wherein the control system further includes a compensating function for delivering a compensating bolus to account for any suspended medication delivery profile.

46. The infusion device of claim 43, wherein the at least two suspend functions further include a full suspend function for directly suspending all fluid delivery.

47. The infusion device of claim 43, wherein the two or more medication delivery profiles are selected from the group including a square wave bolus profile, a dual wave bolus profile and a basal profile.

48. The infusion device of claim 43, wherein the at least two suspend functions include a menu system for selecting a period of time for temporarily suspending fluid delivery by the infusion device.

49. The infusion device of claim 48, wherein the menu system includes a plurality of fixed periods from which to select as the period of time for temporarily suspending fluid delivery.

50. The infusion device of claim 48, wherein the menu system includes one or more increment periods to increment the period of time for temporarily suspending fluid delivery.

51. The infusion device of claim 48, wherein the menu system includes a specified time of day to select as an end of the period of time for temporarily suspending fluid delivery.

52. The infusion device of claim 48, wherein after the period of time for temporarily suspending fluid delivery by the infusion device has transpired the infusion device resumes fluid delivery.

53. The infusion device of claim 43, wherein the at least two suspend functions include a block function for suspending delivery of the fluid after a potentially harmful amount of fluid is requested by a user and a warning to the user of the potentially harmful amount of fluid.

54. The infusion device of claim 53, wherein the potentially harmful amount of fluid is a bolus.

55. The infusion device of claim 53, wherein the potentially harmful amount of fluid is a bolus requested too soon after a previous bolus is delivered.

56. The infusion device of claim 53, wherein the potentially harmful amount of fluid is too low a total fluid dose for the day.

57. The infusion device of claim 53, wherein the block function is triggered after a fluid measurement integrated over an integration period exceeds a target value.

58. The infusion device of claim 57 wherein the block function is alternately triggered because a second fluid measurement integrated over a simultaneous and overlapping integration period exceeds the target value.

59. The infusion device of claim 57, wherein the integration period is subdivided into a plurality of subperiods and each of the plurality of subperiods is associated with a subtotal representing the fluid delivered and an oldest subtotal of the subperiods is replaced by a newest subtotal of the subperiods.

60. An infusion device for delivering a fluid from a reservoir to the body of a patient, the infusion device comprising:
  a drive mechanism to deliver the fluid from the reservoir to the body of the patient;
  a processor including a control system for controlling delivery of the fluid;
  a memory to store at least one basal rate profile and at least one bolus profile associated with the reservoir;
  an input device to allow the patient to command the processor; and
  a housing that houses at least a portion of the reservoir, at least a portion of the drive mechanism, the processor, the memory and at least a portion of the input device;
  wherein the control system controls fluid delivery from the reservoir in accordance with the at least one basal rate profile and the at least one bolus profile, such that the at least one basal rate profile and the at least one bolus profile can be used to deliver fluid at the same time,
  wherein the control system includes at least two suspend functions capable of separately suspending at least one of the at least one basal rate profile and the at least one bolus profile, wherein each of the at least two suspend functions may be used independently of the other of the at least two suspend functions so that a user can suspend a first delivery profile that delivers a fluid from the reservoir to a user while a second delivery profile continues to deliver the fluid from the reservoir to the user.

61. The infusion device of claim 60, wherein the control system further includes a resume function for selectively restarting each of the at least one basal rate profile and the at least one bolus profile.

62. The infusion device of claim 60, wherein the control system further includes a compensating function for delivering a compensating bolus to account for any suspended at least one basal rate profile and at least one bolus profile.

63. The infusion device of claim 60, wherein the at least two suspend functions further include a full suspend function for directly suspending all fluid delivery.

64. The infusion device of claim 60, wherein the at least one basal rate profile and the at least one bolus profile are selected from the group including a square wave bolus profile, a dual wave bolus profile and a basal profile.

65. The infusion device of claim 60, wherein the at least two suspend functions include a menu system for selecting a period of time for temporarily suspending fluid delivery by the infusion device.

66. The infusion device of claim 65 wherein the menu system includes a plurality of fixed periods from which to select as the period of time for temporarily suspending fluid delivery.

67. The infusion device of claim 65, wherein the menu system includes one or more increment periods to increment the period of time for temporarily suspending fluid delivery.

68. The infusion device of claim 65, wherein the menu system includes a specified time of day to select as an end of the period of time for temporarily suspending fluid delivery.

69. The infusion device of claim 65, wherein after the period of time for temporarily suspending fluid delivery by the infusion device has transpired the infusion device resumes fluid delivery.

70. The infusion device of claim 60, wherein the at least two suspend functions include a block function for suspending delivery of the fluid after a potentially harmful amount of fluid is requested by a user and a warning to the user of the potentially harmful amount of fluid.

71. The infusion device of claim 70, wherein the potentially harmful amount of fluid is a bolus.

72. The infusion device of claim 70, wherein the potentially harmful amount of fluid is a bolus requested too soon after a previous bolus is delivered.

73. The infusion device of claim 70, wherein the potentially harmful amount of fluid is too low a total fluid dose for the day.

74. The infusion device of claim 70, wherein the block function is triggered after a fluid measurement integrated over an integration period exceeds a target value.

75. The infusion device of claim 74, wherein the block function is alternately triggered because a second fluid measurement integrated over a simultaneous and overlapping integration period exceeds the target value.

76. The infusion device of claim 74, wherein the integration period is subdivided into a plurality of subperiods and each of the plurality of subperiods is associated with a subtotal representing the fluid delivered and an oldest subtotal of the subperiods is replaced by a newest subtotal of the subperiods.

77. An infusion device for delivering a fluid from a reservoir to the body of a patient, the infusion device comprising:
   a drive mechanism to deliver the fluid from the reservoir to the body of the patient;
   a processor including a control system for controlling delivery of the fluid;
   a memory to store two or more medication delivery profiles;
   an input device to allow the patient to command the processor; and
   a housing that houses at least a portion of the reservoir, at least a portion of the drive mechanism, the processor, the memory and at least a portion of the input device;
   wherein the two or more medication delivery profiles include at least one basal rate profile and at least one bolus profile,
   wherein the control system controls fluid delivery from the reservoir in accordance with the at least one basal rate profile and the at least one bolus profile, such that the at least one basal rate profile and the at least one bolus profile can be used to deliver fluid at the same time,
   wherein the control system includes at least two suspend functions capable of separately suspending at least one of the two or more medication delivery profiles, such that fluid delivery continues in accordance with at least one of the two or more medication delivery profiles, wherein each of the a least two suspend functions may be used independently of the other of the at least two suspend functions so that a user can suspend a first delivery profile that delivers a fluid from the reservoir to a user while a second delivery profile continues to deliver the fluid from the reservoir to the user.

78. The infusion device of claim 77, wherein the control system further includes a resume function for selectively restarting each of the two or more medication delivery profiles.

79. The infusion device of claim 77, wherein the control system further includes a compensating function for delivering a compensating bolus to account for any suspended medication delivery profiles.

80. The infusion device of claim 77, wherein the at least two suspend functions include a full suspend function for directly suspending all fluid delivery.

81. The infusion device of claim 77, wherein the two or more medication delivery profiles are selected from the group including a square wave bolus profile, a dual wave bolus profile and a basal profile.

82. The infusion device of claim 77, wherein the at least two suspend functions include a menu system for selecting a period of time for temporarily suspending fluid delivery by the infusion device.

83. The infusion device of claim 77, wherein the menu system includes a plurality of fixed periods from which to select as the period of time for temporarily suspending fluid delivery.

84. The infusion device of claim 82, wherein the menu system includes one or more increment periods to increment the period of time for temporarily suspending fluid delivery.

85. The infusion device of claim 82, wherein the menu system includes a specified time of day to select as an end of the period of time for temporarily suspending fluid delivery.

86. The infusion device of claim 82, wherein after the period of time for temporarily suspending fluid delivery by the infusion device has transpired the infusion device resumes fluid delivery.

87. The infusion device of claim 77, wherein the at least two suspend functions include a block function for suspending delivery of the fluid after a potentially harmful amount of fluid is requested by a user and a warning to the user of the potentially harmful amount of fluid.

88. The infusion device of claim 87, wherein the potentially harmful amount of fluid is a bolus.

89. The infusion device of claim 87, wherein the potentially harmful amount of fluid is a bolus requested too soon after a previous bolus is delivered.

90. The infusion device of claim 87, wherein the potentially harmful amount of fluid is too low a total fluid dose for the day.

91. The infusion device of claim 87, wherein the block function is triggered after a fluid measurement integrated over an integration period exceeds a target value.

92. The infusion device of claim 91, wherein the block function is alternately triggered because a second fluid measurement integrated over a simultaneous and overlapping integration period exceeds the target value.

93. The infusion device of claim 91, wherein the integration period is subdivided into a plurality of subperiods and each of the plurality of subperiods is associated with a subtotal representing the fluid delivered and an oldest subtotal of the subperiods is replaced by a newest subtotal of the subperiods.

94. The system of claim 1, wherein the infusion pump is disposed within a housing adapted to he worn on a belt, adapted to be worn under clothing, adapted to be worn against the skin or adapted to fit in a clothing pocket.

95. The method of claim 19, wherein the infusion pump is disposed within a housing adapted to be worn on a belt, adapted to be worn under clothing, adapted to be worn against the skin or adapted to fit in a clothing pocket.

96. The device of claim 43, wherein the infusion pump is disposed within a housing adapted to be worn on a belt, adapted to be worn under clothing, adapted to be worn against the skin or adapted to fit in a clothing pocket.

97. The device of claim 60, wherein the infusion pump is disposed within a housing adapted to be worn on a belt, adapted to be worn under clothing, adapted to be worn against the skin or adapted to fit in a clothing pocket.

98. The device of claim 77, wherein the infusion pump is disposed within a housing adapted to be worn on a belt, adapted to be worn under clothing, adapted to be worn against the skin or adapted to fit in a clothing pocket.

* * * * *